US012569349B2

(12) United States Patent
Fresneau et al.

(10) Patent No.: US 12,569,349 B2
(45) Date of Patent: Mar. 10, 2026

(54) DUAL-ACTION EXPANDABLE INTERVERTEBRAL IMPLANTS

(71) Applicant: Highridge Medical, LLC, Westminster, CO (US)

(72) Inventors: Aymeric Fresneau, Bordeaux (FR); Nicolas Roche, Saint Medard en Jalles (FR); David Rigotto, Saint Selve (FR)

(73) Assignee: Highridge Medical, LLC, Westminster, CO (US)

( * ) Notice: Subject to any disclaimer, the term of this patent is extended or adjusted under 35 U.S.C. 154(b) by 1039 days.

(21) Appl. No.: 17/543,338

(22) Filed: Dec. 6, 2021

(65) Prior Publication Data

US 2022/0175547 A1 Jun. 9, 2022

Related U.S. Application Data

(60) Provisional application No. 63/123,347, filed on Dec. 9, 2020.

(51) Int. Cl.
*A61F 2/44* (2006.01)
*A61F 2/30* (2006.01)

(52) U.S. Cl.
CPC .. *A61F 2/4455* (2013.01); *A61F 2002/30471* (2013.01); *A61F 2002/30556* (2013.01); *A61F 2002/30579* (2013.01); *A61F 2002/30904* (2013.01)

(58) Field of Classification Search
CPC ...... A61F 2/44–447; A61F 2002/30471; A61F 2002/30556; A61F 2002/30579; A61F 2002/30904; A61F 2002/30266
See application file for complete search history.

(56) References Cited

U.S. PATENT DOCUMENTS

| | | | |
|---|---|---|---|
| 10,561,502 B2 | 2/2020 | Bernard et al. | |
| 10,624,756 B2 | 4/2020 | Bernard et al. | |
| 10,631,996 B2 | 4/2020 | Bernard et al. | |
| 2007/0282441 A1* | 12/2007 | Stream ................... | A61B 17/92 623/17.11 |
| 2014/0114420 A1* | 4/2014 | Robinson ................ | A61F 2/447 623/17.16 |

(Continued)

OTHER PUBLICATIONS

Extended European Search Report for European Patent Application No. 21213489.4, dated Sep. 5, 2022 9 pages.

(Continued)

*Primary Examiner* — Nicholas J Plionis

(57) ABSTRACT

A two-stage intervertebral implant comprises an expandable cage comprising a pivot connecting upper and lower bodies, a first expansion mechanism, such as a wedge, configured to pivot the upper body and the lower body at the pivot point in a first stage, and a second expansion mechanism, such as a toggle joint, configured to pivot the upper body and the lower body at the pivot point in a second stage beyond the first stage. A method of implanting an implant comprises inserting the implant into anatomy, the implant comprising a first component rotatably coupled to a second component at a pivot point, operating a first expansion mechanism to rotate the implant at the pivot point to expand the implant to a first level, and operating a second expansion mechanism to rotate the implant at the pivot point from the first level to a second level.

20 Claims, 23 Drawing Sheets

(56) References Cited

U.S. PATENT DOCUMENTS

| | | | |
|---|---|---|---|
| 2015/0148908 A1 | 5/2015 | Marino et al. | |
| 2016/0166396 A1* | 6/2016 | McClintock | A61F 2/446 |
| | | | 623/17.16 |
| 2016/0331542 A1* | 11/2016 | Faulhaber | A61F 2/4611 |
| 2016/0354212 A1 | 12/2016 | Baynham | |
| 2017/0112630 A1* | 4/2017 | Kuyler | A61F 2/4455 |
| 2020/0054461 A1* | 2/2020 | Marrocco | A61F 2/4425 |
| 2020/0129307 A1 | 4/2020 | Hunziker et al. | |
| 2020/0360151 A1 | 11/2020 | Kuyler et al. | |

OTHER PUBLICATIONS

Official Action for European Patent Application No. 21213489.4, dated Feb. 14, 2025 5 pages.

* cited by examiner

502 — Attach collapsed implant to inserter

504 — Insert implant between anatomy

506 — Insert driver into threaded fastener

508 — Commence 1st stage expansion

510 — Rotate threaded fastener

512 — Drive wedge along surfaces

514 — Engage wedge with stop

516 — Commence 2nd stage expansion

518 — Engage toggle joint

520 — Expand to desired angle

522 — Remove driver

524 — Remove inserter

526 — Implant bone cement

528 — Close incision

500

DUAL-ACTION EXPANDABLE INTERVERTEBRAL IMPLANTS

CLAIM OF PRIORITY

This application claims the benefit of U.S. Provisional Patent Application Ser. No. 63/123,347, filed on Dec. 9, 2020, the benefit of priority of which is claimed hereby, and which is incorporated by reference herein in its entirety.

TECHNICAL FIELD

This document pertains generally, but not by way of limitation, to implants for positioning between adjacent bones, such as can be used in spinal correction procedures. More specifically, but not by way of limitation, the present application relates to intervertebral implants that are expandable.

BACKGROUND

A spinal column can require correction of spinal deformities and abnormalities resulting from trauma or degenerative issues. Various methods of correcting issues with the spinal column can include fusing adjacent vertebrae together with a spacer and/or a rod system to immobilize the degenerated portion of the spine. Such procedures can be beneficial in patients having diseased or degenerated disc material between the vertebrae. For example, intervertebral implants can be positioned between adjacent vertebrae to fuse the vertebrae together, after disk material located therebetween is removed. In order to facilitate insertion between the adjacent vertebrae, the implants can be configured to expand. As such, the implant can be collapsed to have a smaller height for insertion and after being positioned into the target anatomy can be expanded to a taller height to provide the desired spacing. It can, however, be difficult to expand the implant to the desired level due to, for example, resistance from the anatomy.

Examples of intervertebral spacer implants are described in Pub. No. US 2015/0148908 to Marino et al.; Pub. No. US 2016/0354212 to Baynham; and Pub. No. US 2020/0129307 to Hunziker et al.

Overview

The present inventors have recognized, among other things, that a problem to be solved can include the difficulty of providing expandable intervertebral implants that simultaneously provide bone support to the adjacent bones, and that are easy to expand when implanted. In particular, the present inventors have recognized that many typical expandable implants utilize only a single mechanism to expand the implant. As such, each of these implants typically include tradeoffs between providing bone support, expansion height and mechanical advantage. For example, some intervertebral implants can be configured to be expanded using a wedge system. Wedge-based expanders can provide strong bone support between bones. However, wedge expanders can be limited in the amount they can be expanded, e.g., wedges-based expanders typically do not provide a large expansion height.

The present subject matter can help provide a solution to these problems, such as by providing an interbody implant that is configured to expand using two different expansion mechanisms. The two different expansion mechanisms can be configured to be deployed in a staged or staggered manner such that advantageous of each mechanism can be taken advantage of during different states of expansion. For example, a first expansion mechanism having a greater opening strength or force (e.g., a greater mechanical advantage) can be used to initiate expansion, while a second expansion mechanism having a greater expansion height can be used to provide further expansion. In examples, the expansion mechanisms can be configured to work cooperatively, e.g., at the same time, and then exclusively, e.g., one at a time. In other examples, the expansion mechanisms can be configured to operate sequentially, e.g., one and then the other. In examples, a wedge expander and a toggle joint expander can be paired together. The wedge expander can be configured to operate first to provide the force necessary to overcome high loading initially placed on the implant by the anatomy. The toggle joint expander can be configured to take over from the wedge expander to provide additional expansion beyond what is provided by the wedge expander.

In an example, an intervertebral implant can comprise a first cage, a second cage, a hinge connecting the first cage and the second cage at a first side of the intervertebral implant, a toggle joint connecting the first cage and the second cage at a second side of the intervertebral implant, and a wedge positioned between the first cage and the second cage and configured to translate from proximate the first side toward the second side to cause rotation about the hinge and initial expansion of the toggle joint.

In another example, a method of inserting an intervertebral implant can comprise inserting the intervertebral implant into anatomy of a patient, the intervertebral implant comprising a first component rotatably coupled to a second component at a pivot point, operating a first expansion mechanism to rotate the intervertebral implant at the pivot point to expand the intervertebral implant to a first level, and operating a second expansion mechanism to rotate the intervertebral implant at the pivot point from the first level to a second level.

In an additional example, a two-stage intervertebral implant can comprise an expandable cage comprising an upper body, a lower body, and a pivot connecting the upper body and the lower body, a first expansion mechanism configured to pivot the upper body and the lower body at the pivot point in a first stage, and a second expansion mechanism configured to pivot the upper body and the lower body at the pivot point in a second stage beyond the first stage.

In another example, an inserter device for a prosthetic implant can comprise an elongate rod extending from a proximal end to a distal end and including an internal lumen extending between the proximal end and the distal end and a first channel extending along an exterior of the elongate rod between the proximal end and the distal end, a first coupling arm comprising an elongate shank configured to ride in the first channel, a distal coupling portion including a coupling feature configured for coupling to the prosthetic implant and a proximal actuation portion, and an actuation mechanism coupled to a proximal end of the elongate rod and configured to move the first coupling arm within the first channel between a retracted position and an advanced position.

In an additional example, a push mechanism for dispensing a material from a handheld dispenser with a piston can comprise a trigger configured to rotate about a pivot point, a first pawl configured to rotate on the trigger a first distance from the pivot point, and a second pawl configured to rotate on the trigger a second distance from the pivot point, wherein the second pawl is positioned relative to the first pawl to form a channel therebetween for pushing the piston in a longitudinal direction, wherein the first pawl and the second pawl are oppositely configured to interact with the channel.

This overview is intended to provide an overview of subject matter of the present patent application. It is not intended to provide an exclusive or exhaustive explanation of the invention. The detailed description is included to provide further information about the present patent application.

Figure 1:
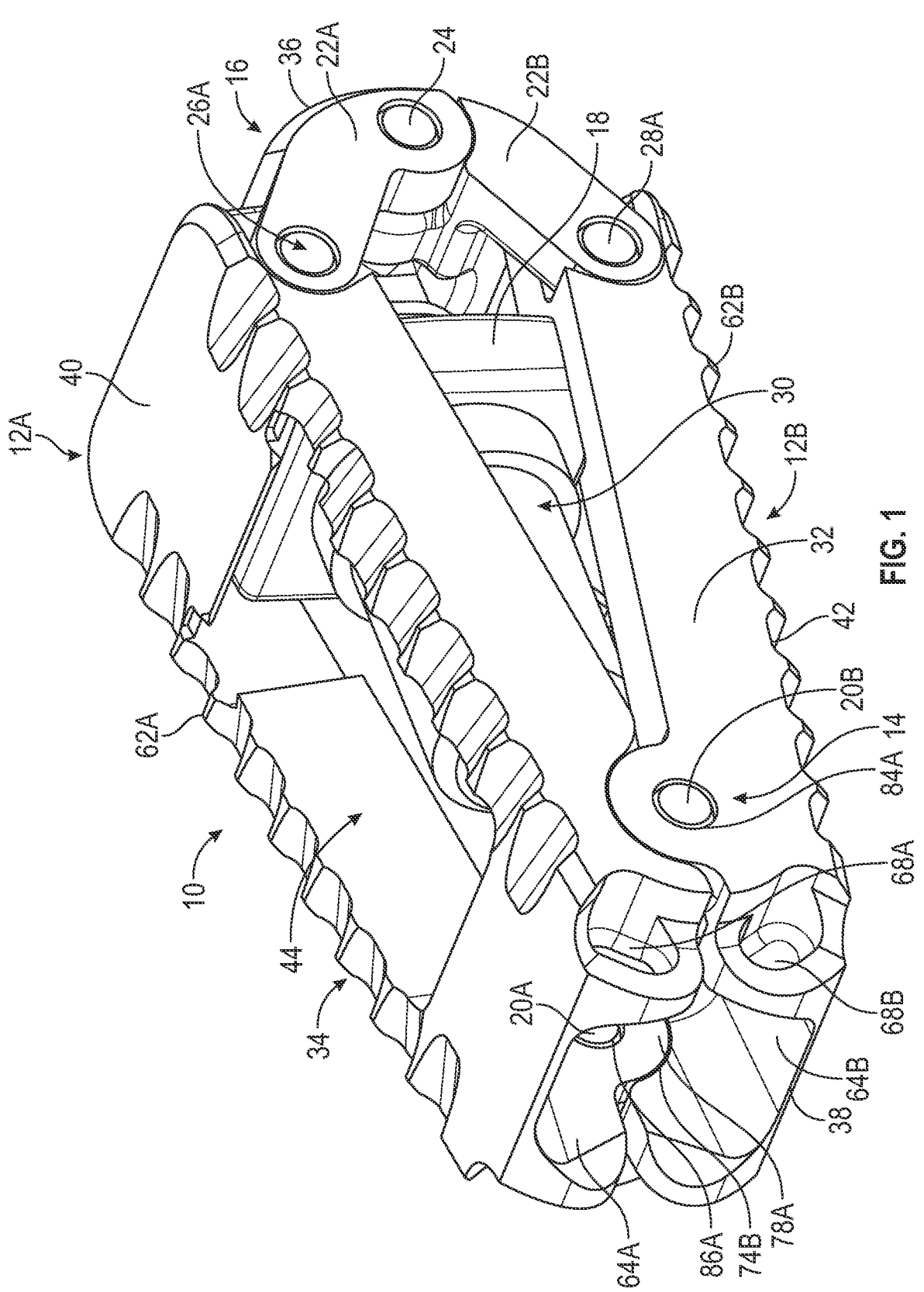
FIG. 1 is a perspective view of an interbody implant of FIG. 1 comprising a cage structure pivotable by a wedge and a toggle joint.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 2A:
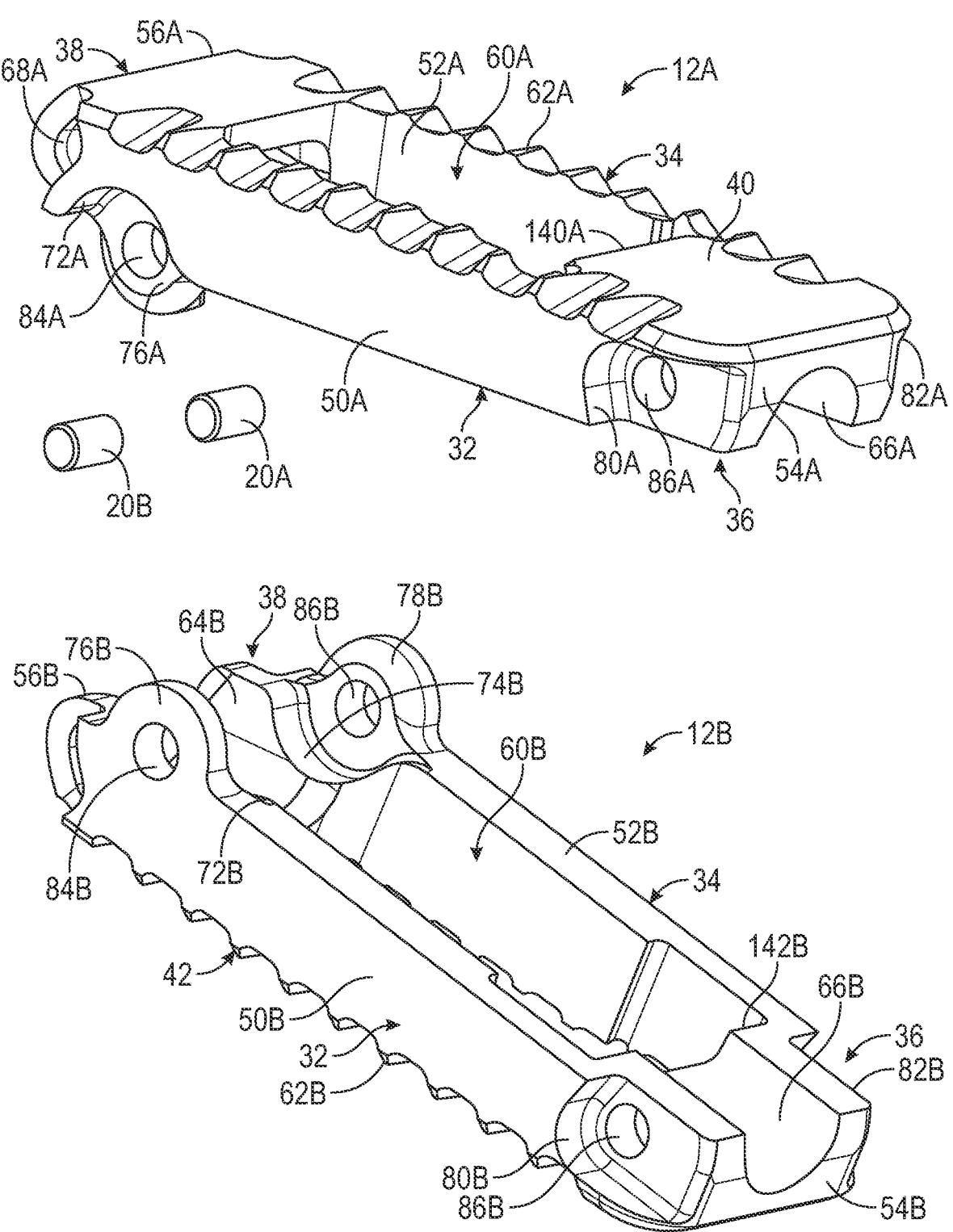
FIG. 2A is an exploded view of the interbody implant of FIG. 1 showing superior and inferior cages of the cage structure and pivot pins.
Figure 2B:
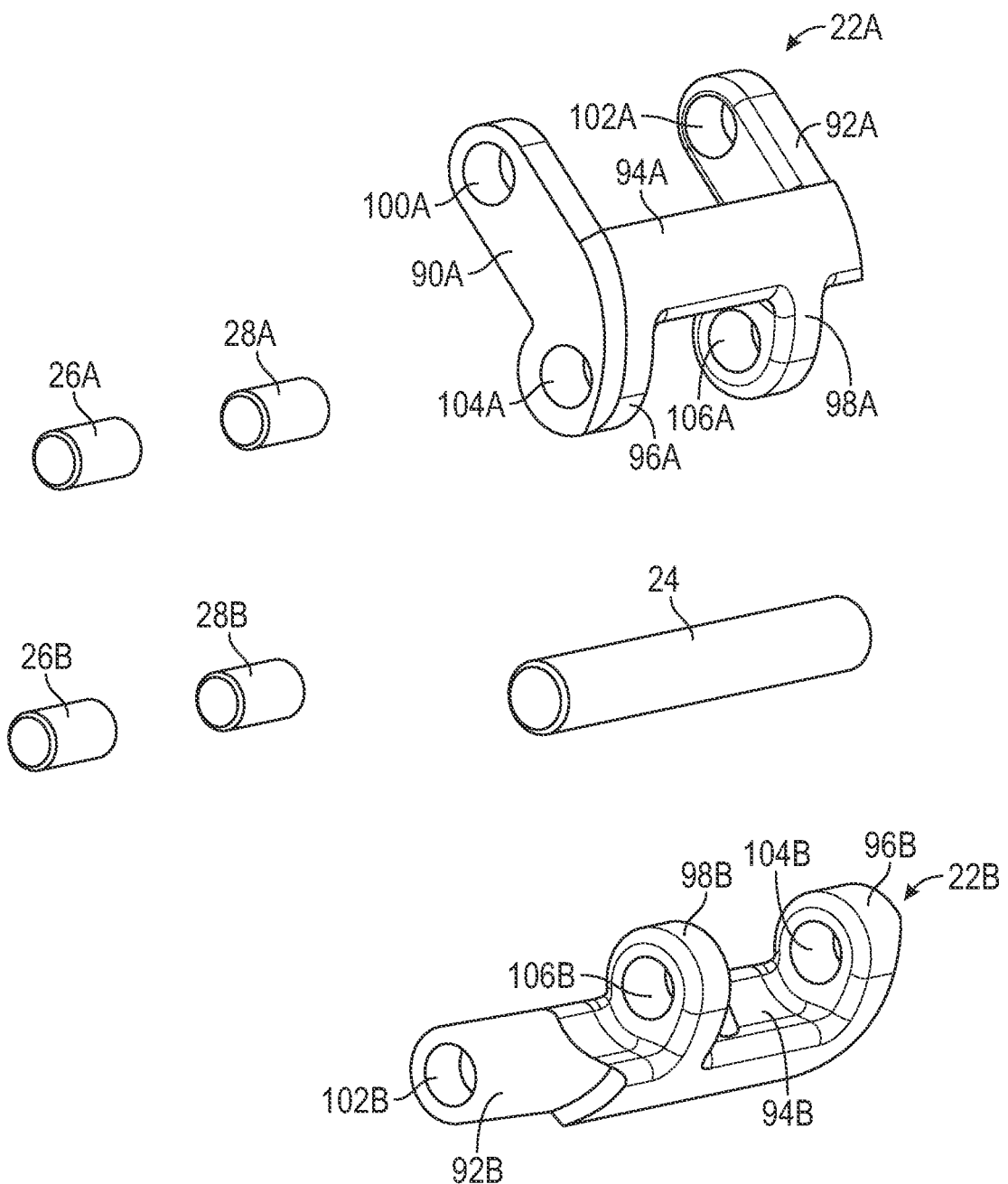
FIG. 2B is an exploded view of the interbody implant of FIG. 1 showing the toggle joint and associated pins.
Figure 2C:
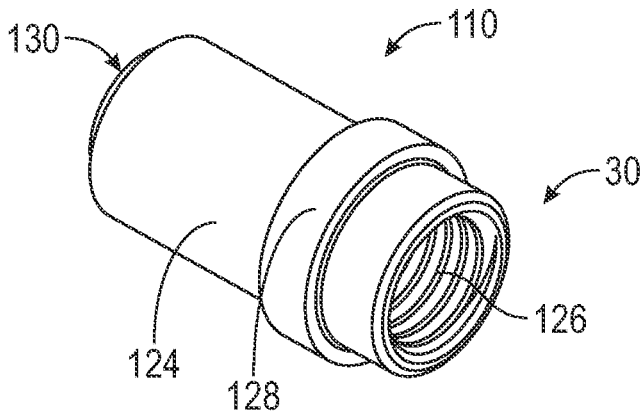
FIG. 2C is an exploded view of the interbody implant of FIG. 1 showing the wedge and a threaded fastener.
Figure 2C:
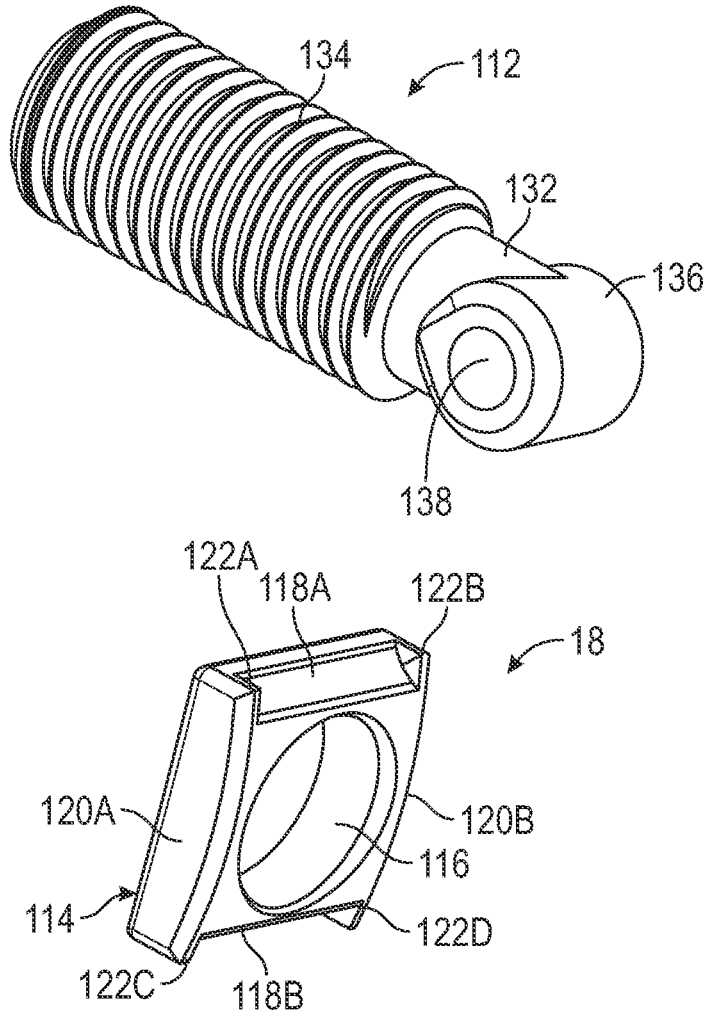

FIG. 1 is a perspective view of interbody implant 10 of the present application showing superior cage 12A, inferior cage 12B, hinge or pivot joint 14, toggle joint 16 and wedge 18. FIG. 2A is an exploded view of interbody implant 10 of FIG. 1 showing superior cage 12A and inferior cage 12B. FIG. 2B is an exploded view of interbody implant 10 of FIG. 1 showing toggle joint 16. FIG. 2C is an exploded view of interbody implant 10 of FIG. 1 showing wedge 18 and screw mechanism or drive shaft 30.

Figure 3A:
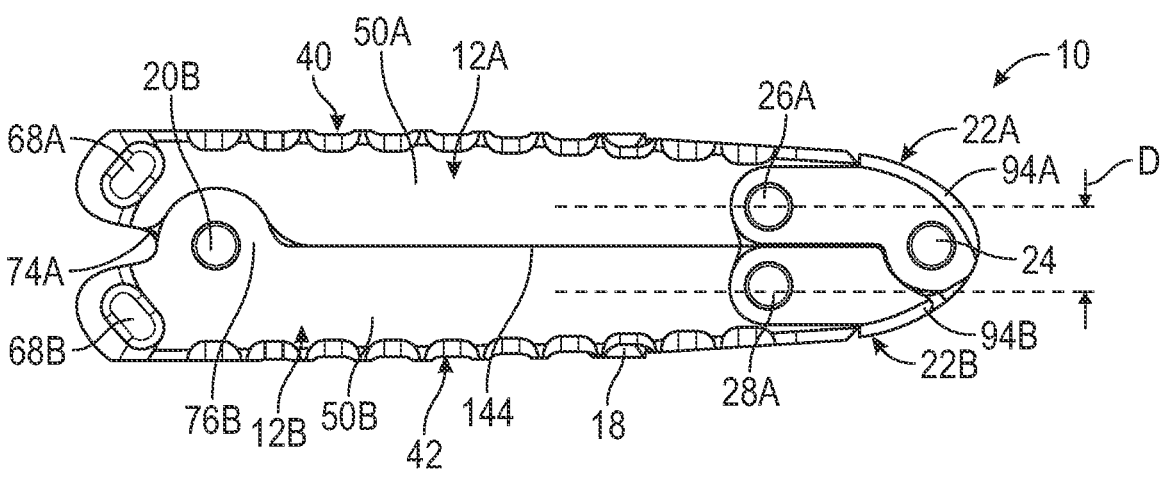
FIG. 3A is a side view of the interbody implant of FIG. 1 in a collapsed state showing interior surfaces of the superior and inferior cages engaged with each other.
Figure 3B:
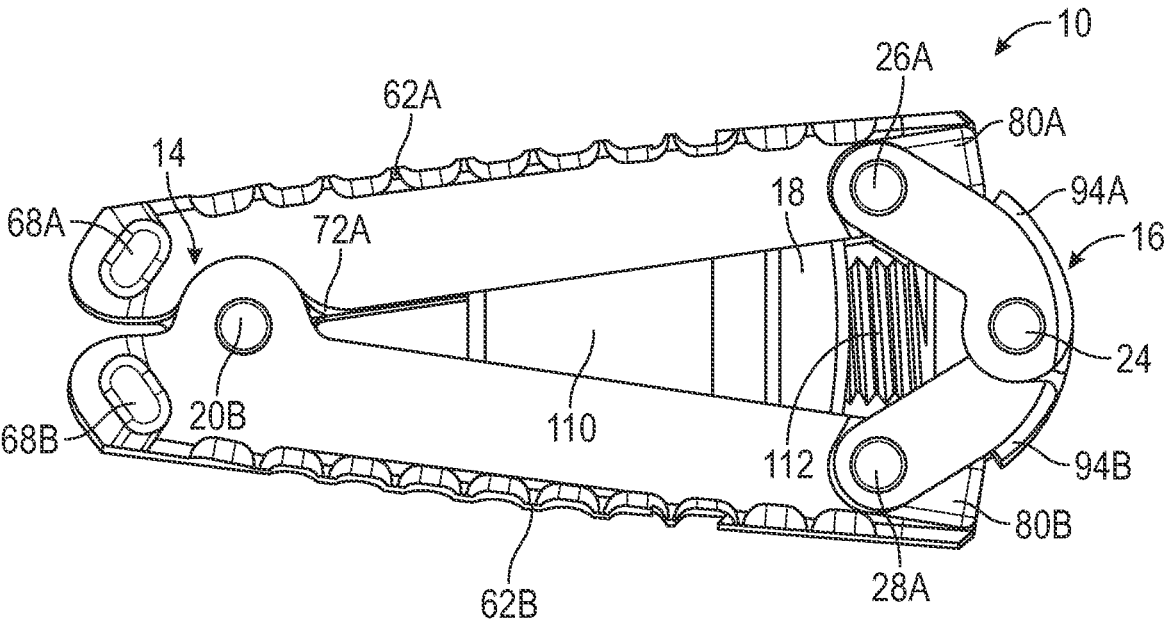
FIG. 3B is a side view of the interbody implant of FIG. 1 in an expanded state showing interior surfaces of the superior and inferior cages angled relative to each other.

FIG. 3A is a side view of interbody implant 10 of FIG. 1 in a collapsed state showing interior surfaces of superior and inferior cages 12A and 12B engaged with each other. FIG. 3B is a side view of interbody implant 10 of FIG. 1 in an expanded state showing interior surfaces of superior and inferior cages 12A and 12B angled relative to each other.

Figures 4, 5:
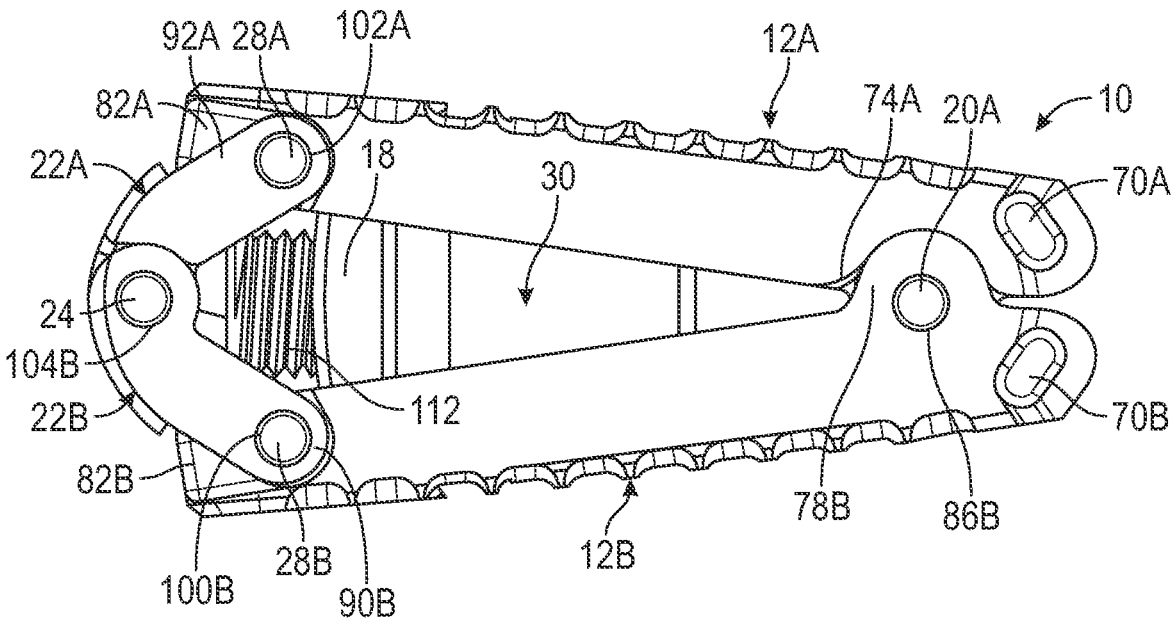
FIG. 4 is a side view of the interbody implant of FIG. 3B from an opposing viewpoint.
FIG. 5 is a top view of the interbody implant of FIG. 3B showing the threaded fastener through windows of the cage structure.
Figure 6:
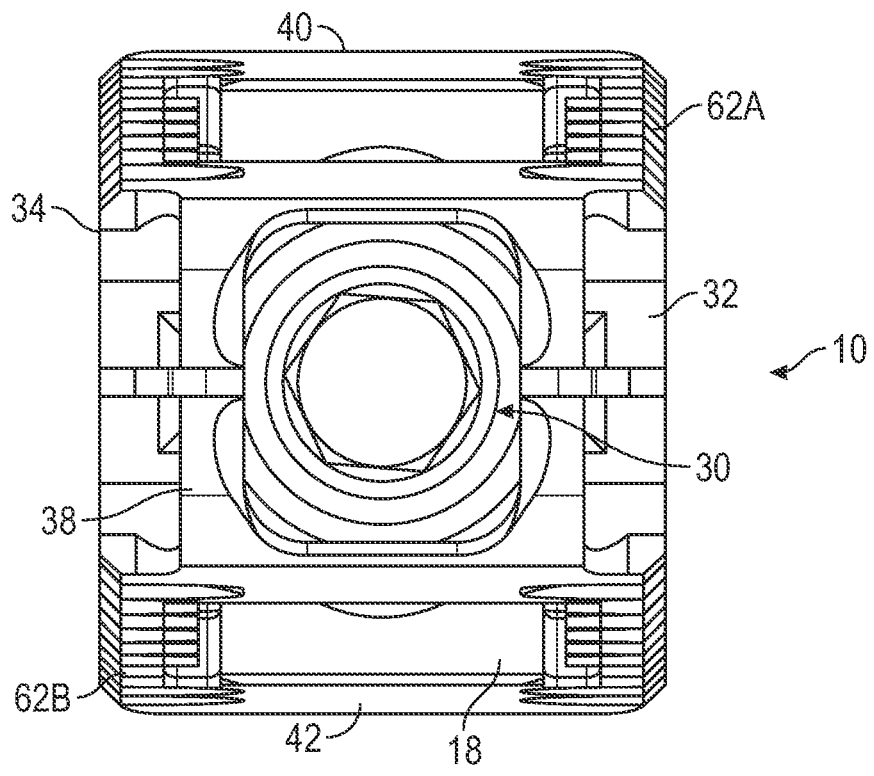
FIG. 6 is an end view of the interbody implant of FIG. 1 showing the threaded fastener for the wedge and the toggle joint.

FIG. 4 is a side view of interbody implant 10 of FIG. 3B from an opposing viewpoint of that of FIG. 3B. FIG. 5 is a top view of interbody implant 10 of FIG. 3B showing drive shaft 30 through windows 60A and 60B of the cage structure.

Figure 7:
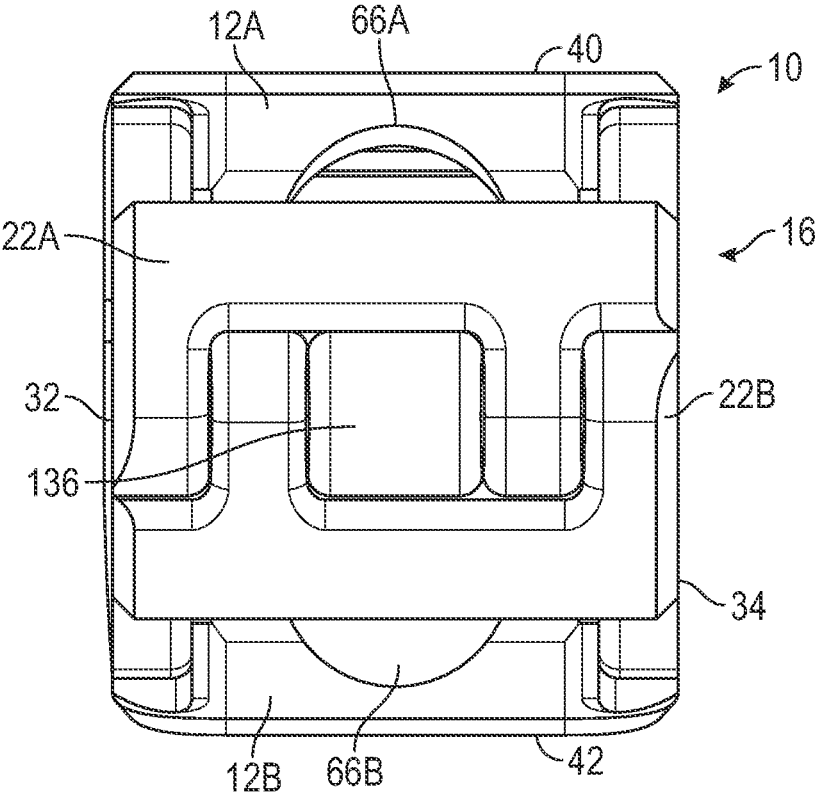
FIG. 7 is an end view of the interbody implant of FIG. 1 showing the toggle joint.
Figures 8A, 8B, 8C:
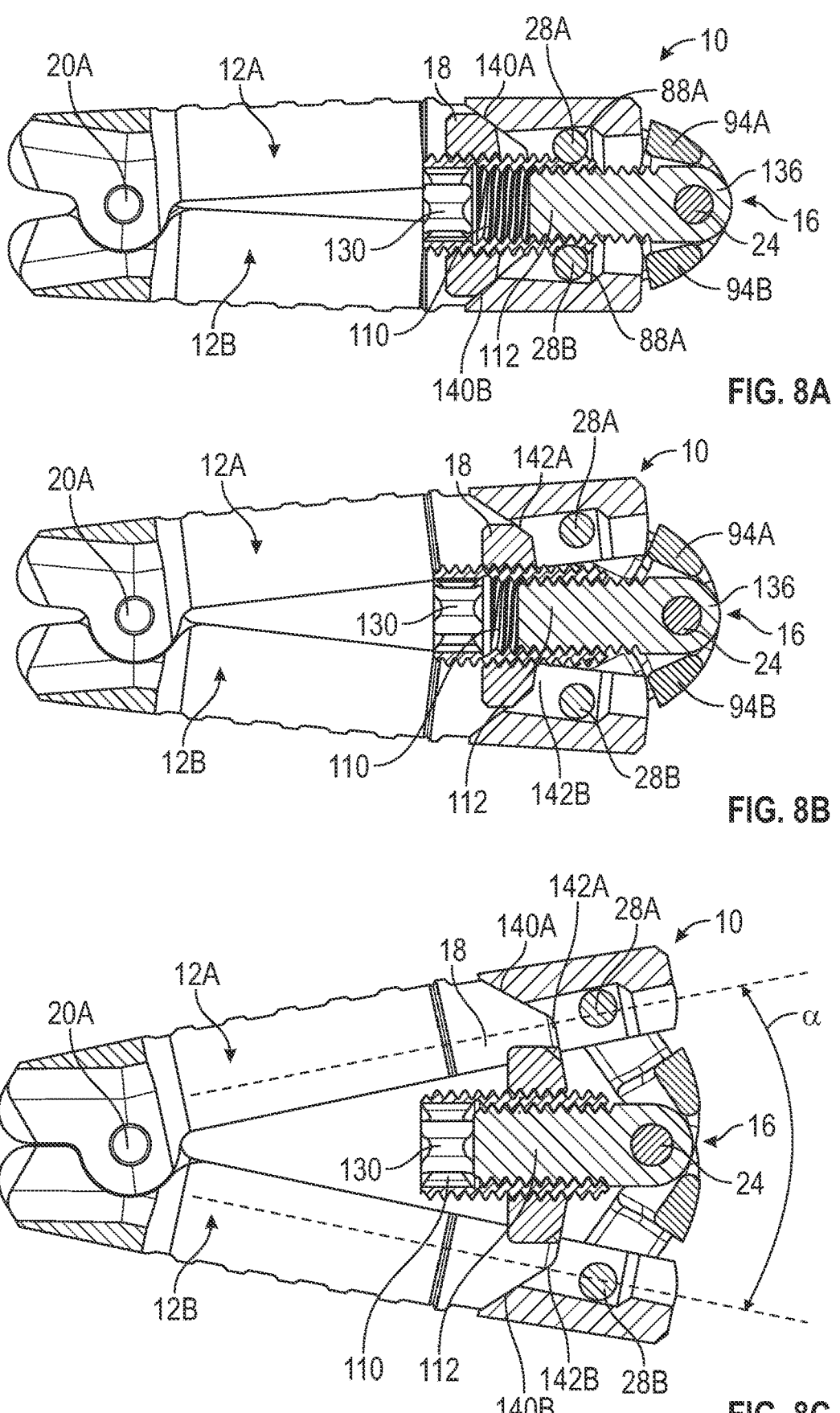
FIG. 8A is a side cross-sectional view of the interbody implant of FIG. 4 in a substantially collapsed state.
FIG. 8B is a side cross-sectional view of the interbody implant between the collapsed state and the expanded state showing the wedge disengaging and the toggle joint engaging.
FIG. 8C is a side cross-sectional view of the interbody implant of FIG. 2 in a substantially expanded state.

FIG. 7 is an end view of interbody implant 10 of FIG. 1 showing toggle joint 16. FIG. 8A is a side cross-sectional view of interbody implant 10 of FIG. 4 in a substantially collapsed state.

FIGS. 1-7 show the various features of implant 10 from different angles, different states of being exploded and different operational states and together show the configuration and operation of implant 10. FIGS. 1-7 are discussed concurrently.

Superior cage 12A and inferior cage 12B can be connected at pivot joint 14 via pins 20A and 20B. Toggle joint 16 can comprise superior linkage 22A and inferior linkage 22B, which can be connected to each other via pin 24. Superior linkage 22A can be connected to superior cage 12A via pin 26A and pin 28A (FIG. 2B). Inferior linkage 22B can be connected in inferior cage 12B via pin 26B and pin 28B (FIG. 2B). Wedge 18 can be configured to interact with superior cage 12A, inferior cage 12B and toggle joint 16 via drive shaft 30.

Interbody implant 10 can comprise side surface 32, side surface 34, insertion portion 36, coupling portion 38, superior surface 40 and inferior surface 42. With reference to FIGS. 1-8C, the present application shows and describes a particular orientation of interbody implant 10. However, other orientations can be used. For example, coupling portion 38 and insertion portion 36 can be on either the anterior or posterior side of the spinal column; e.g., interbody implant 10 can be rotated one-hundred-eighty degrees in the plane of FIGS. 3A and 3B. Likewise, superior surface 40 and inferior surface 42 can be reversed so superior surface 40 point downward an inferior surface points upward, e.g., interbody implant 10 can be rotated one-hundred-eighty degrees in the plane of FIGS. 6 and 7. Additionally, side surfaces 32 and 34 can be used in opposite directions.

Interbody implant 10 can be shaped for positioning between adjacent anatomic bodies, such as adjacent vertebrae in a spinal column. Interbody implant can be configured to occupy space where a degenerative or damaged disk has been removed. As such, interbody implant 10 can be configured to directly contact bone, particularly at superior surface 40 and inferior surface 42. For example, superior surface 40 can contact the inferior surface of an upper vertebra and inferior surface 42 can contact the superior surface of a lower vertebra. Interbody implant 10 can be configured to promote bone in-growth into the surfaces of interbody implant 10 by inclusion of space between superior cage 12A and inferior cage 12B, and elsewhere, that can form internal cavity 44, which can provide a space for holding bone graft or other bone-growth-promoting materials to promote in-growth of bone from the adjacent vertebrae.

As is discussed in greater detail below with reference to FIGS. 3A and 3B, interbody implant 10 can be collapsed to the configuration of FIG. 3A to facilitate insertion into anatomy of a patient, such as through an incision and in between adjacent bones, and then expanded to the configuration of FIG. 3B when positioned in the desired location to, for example, influence the relative position of the adjacent bone. As is discussed in greater detail with reference to FIGS. 8A-8C, drive shaft 30 can be operated to change interbody implant 10 between the expanded configuration of FIG. 3B and the collapsed position of FIG. 3A, and vice versa, in a staged or staggered manner to utilize the different mechanical advantages of wedge 18 and toggle joint 16.

Superior cage 12A can comprise first leg 50A, second leg 52A, insertion end 54A and coupler end 56A. Inferior cage 14B can comprise first leg 50B, second leg 52B, insertion end 54B and coupler end 56B. Legs 50A and 52A and ends 54A and 56A can be configured to define superior surface 40 and surround window 60A. Legs 50B and 52B and ends 54B and 56BA can be configured to define inferior surface 42 and surround window 60B.

Superior cage 12A can further comprise scallops 62A, portal 64A, portal 66A (FIG. 2A) and couplers 68A and 70A (FIG. 4). Inferior cage 12B can further comprise scallops 62B, portal 64B, portal 66B (FIG. 2A) and couplers 68B and 70B (FIG. 4). Superior cage 12A can comprise outer hinge pockets 72A and 74A (FIG. 4) and inner hinges 76A and 78A (FIG. 1). Inferior cage 12B can include inner hinge pockets 72B and 74B and outer hinges 76B and 78B. Superior cage 12A can comprise toggle pockets 80A and 82A and inferior cage 12B can comprise toggle pockets 80B and 82B.

Legs 50A-52B can include comprise elongate bodies configured to extend in anterior-posterior directions and provide structural stability to implant 10. Scallops 62A and 62B can be provided on legs 50A-52B to provide engagement with soft tissue and bone, such as when implant 10 is in an expanded state. Legs 50A and 52A can be connected by insertion end 54A and coupler end 56A to form portal 64A. Superior surface 40 and inferior surface 42 can include flat or planar portions to allow implant to slide along soft tissue or bone, such as when implant 10 is in a collapsed state. Portals 64A and 64B can extend into the superior and inferior surfaces of implant 10 to form a superior-inferior path through implant 10, thereby allowing bone-growth through implant 10.

Portals 64A and 64B and 66A and 66B can cooperate to form a medial-lateral passage through implant 10. Portals 66A and 66B can provide space for operation of toggle joint 16. Portals 64A and 64B can provide space for an instrument to reach drive shaft 30 for wedge 18. Portals 64A and 64B can also provide access to internal cavity 44 for the placement of bone graft material, bone cement or the like.

Couplers 68A-70B can form sockets for coupling to a tool, such as a four-pin insertion device (e.g., inserter 600 of FIG. 10) having four circular pins or pads (e.g., couplers 816A, 816B, 818A, 818B of FIG. 20B) that can engage couplers 68A-78B. Couplers 68A-70B can have an arcuate shape to allow for articulation of superior cage 12A and inferior cage 12B while remaining engaged with the four pins of the insertion device. Thus, the pads or pins of the insertion device can be circular and have a diameter that is equal to the width of the slots forming couplers 68A-70A, but the slots can be longer to allow the pads or pins to slide in the slots. The pads or pins can be mounted to spring-loaded detents to allow for engagement with couplers 68A-70B, but that prevent relative rotation between the insertion device and implant 10. Thus, the insertion device can be used to push implant 10 between anatomy and position implant 10 in the desired location.

Superior cage 12A and inferior cage 12B can be similarly constructed except for the locations of pockets 72A and 74A and pockets 72B and 74B. Pockets 72A and 74A of superior cage 12A can be configured to be exposed to the exterior of implant 10, while flanges 76B and 78B of inferior cage 12B can be configured to be exposed to the exterior of implant 10. Conversely, pockets 72B and 74B of inferior cage 12B can be configured to be exposed to the interior of implant 10, while flanges 76A and 78A of superior cage 12A can be configured to be exposed to the interior of implant 10. As such, flanges 76A and 78A of superior cage 12A can nest within flanges 76B and 78B of inferior cage 12B. Pin bores 84A and 86A can align with pin bores 84B and 86B to receive pins 20A and 20B, respectively. As such, superior cage 12A and inferior cage 12B can pivot relative to each other at pivot joint 14.

Toggle pockets 80A-82B can cooperate to receive linkages 22A and 22B. Toggle pockets 80A-82B can include pin bores 86A and 86B and 88A (FIG. 8A) and 88B (FIG. 8A), respectively, to receive pins 26A, 28A, 26B and 28B. Superior linkage 22A can comprise first link, 90A, second link 92A, crosspiece 94A, first cam 96A, second cam 98A and pin holes 100A, 102A, 104A and 106A. Inferior linkage 22B can comprise first link, 90B, second link 92B, crosspiece 94B, first cam 96B, second cam 98B and pin holes 100B, 102B, 104B and 106B.

Link 90A can be positioned in pocket 80A, link 92A can be positioned in pocket 82A, link 90B can be positioned in pocket 80B and link 92B can be positioned in pocket 82B. Superior linkage 22A and inferior linkage 22B can be configured to have the same shape, but are used in opposite orientations. As such, pin holes 104A, 106B, 104B and 106A can align to receive pin 24.

Leg 90A and cam 96A can be offset from each other and leg 92A and cam 98A can be offset from each other such that linkage 22A has a curved shape. Leg 90B and cam 96B can be offset from each other and leg 92B and cam 98B can be offset from each other such that linkage 22B has a curved shape. Likewise, crosspieces 94A and 94B can be curved in a corresponding manner. Thus, linkages 22A and 22B can be tucked between cages 12A and 12B in the collapsed state to provide a low profile. Additionally, the curvature of linkages 22A and 22B give insertion portion 36 implant 10 a pointed shape in the collapsed state as can be seen in FIG. 3A and a rounded shape in the expanded state as can be seen in FIG. 3B.

Drive shaft 30 can comprise first shaft 110 and second shaft 112. Wedge 18 can comprise body 114, socket 116, slide surface 118, side surfaces 120A and 120B, and stops 122A-122D. First shaft 110 can comprise shaft 124, interior passage 126, flange 128 and drive socket 130. In various examples, such as those of FIGS. 8A-8C, flange 128 can be omitted. Second shaft 112 can comprise shaft 132, threaded exterior 134, coupler 136 and pin hole 138. In an example, interior passage 126 and threaded exterior 134 can be threadedly engaged with each other in similar fashion as the fastener known as a binding post.

Wedge 18 can be positioned on first shaft 110 such that socket 116 abuts flange 128. In the illustration of FIG. 2C, socket 116 of wedge 18 can comprise a throughbore and the exterior of shaft 124 can be smooth so that first shaft 110 can rotate within wedge 18. However, in additional examples, as shown in FIGS. 8A-8C, socket 116 and the exterior of shaft 124 can be mated in a threaded engagement. In such a configuration, drive shaft 30 can be configured to provide dual-action advancement of wedge 18 relative to toggle joint 16. For example, wedge 18 can ride on the exterior of shaft 124 of first shaft 110 in a threaded engagement and threaded exterior 134 of second shaft 112 can ride in threading of interior passage 126 of first shaft 110. As such, rotation of first shaft 110 at socket 130 via a driver instrument can cause advancement of wedge 18 in a compound fashion. Thus, as discussed with reference to FIGS. 8A-8C, a driver instrument can be inserted into socket 130 to rotate first shaft 110, thereby causing wedge 18 to move closer to second shaft 112 (providing the wedge action) and advancing second shaft 112 into interior passage 126 (facilitating operation of toggle joint 16). Both of these actions bring wedge 18 closer to coupler 136, which ultimately allows toggle joint 16 to operate, such as when stops 122A-122D of wedge 18 engage stop surfaces 142A and 142B of cages 12A and 12B.

The orientation between superior surface 40 and inferior surface 42 can be selected and set such that angle α can correspond to a desired wedge angle (e.g., lordosis) between adjacent vertebrae. For example, interbody implant 10 depicted in FIGS. 1-8C can be configured for use in the lower lumbar region of the spine between any of the L1-L5 vertebrae. In a particular example, interbody implant 10 can be used between the L4 and L5 vertebrae or the L5 and S1 vertebrae where the wedge angle can be in the range of about 6 degrees to about 10 degrees. However, in other embodiments, interbody implant 10 can be configured for use in other regions of a spinal column and can be configured such that superior surface 40 and inferior surface 42 are approximately parallel. Furthermore, intervertebral implants according to the present disclosure can be configured for insertion into the spine at different levels and at different insertion approaches, e.g., anterior or posterior, and with angle α being in the range of approximately fifteen to thirty-five degrees.

FIGS. 8A-8C show cross-sectional views of implant 10 transitioning from a collapsed state to an expanded state via engagement of first and second expansion mechanisms, such as wedge 18 and toggle joint 16. FIGS. 8A-8C are taken at section 8-8 of FIG. 4, with drive shaft 30 additionally being shown in cross-section.

FIG. 8A is a side cross-sectional view of interbody implant 10 of FIG. 4 in the collapsed state. Drive shaft 30 can be retracted so that superior cage 12A and inferior cage 12B are engaged with each other, as shown in FIG. 3A, at interface 144. Also shown in FIG. 3A is distance D, which is the distance between pins 26A and 26B when the interior surfaces of cages 12A and 12B are in contact with each other and parallel.

Drive shaft 30 can be operated so that wedge 18 engages surfaces of superior cage 12A and inferior cage 12B such that wedge 18 causes cages 12A and 12B to spread apart and pivot relative to each other at pin 20B. In particular, surfaces 118A and 118B of wedge 18 can engage angled surfaces 140A and 140B. As first shaft 110 is rotated, wedge 18 can be pushed into angled surfaces 140A and 140B to force superior cage 12A and inferior cage 12B away from each other. Drive shaft 30 can advance wedge 18 twice as fast as the threaded engagement between wedge 18 and first shaft 110 would allow due to the compound threading action arising from second shaft 112 also being threaded into first shaft 110. Thus, wedge 18 can be used to provide the initial angulation between cages 12A and 12B when it is most difficult to displace anatomy.

FIG. 8B is a side cross-sectional view of interbody implant 10 between the collapsed state and the expanded stage showing wedge 18 disengaging angled surfaces 140A and 140B and toggle joint 16 beginning to engage. Wedge 18 can advance toward stop surfaces 142A and 142B along angled surfaces 140A and 140B due to the square outer shape of wedge 18 being prevented from rotation vias surfaces of cages 12A and 12B, thereby allowing the threading engagement to translate wedge 18. In the example of FIG. 2C, instead of wedge 18 being driven along shaft 124 via threaded engagement, wedge 18 can be pulled along by threaded engagement between interior passage 126 and threaded exterior 134 due to flange 128. Wedge 18 can reach the end of angled surfaces 140A and 140B to reach engagement with stop surfaces 142A and 142B. Thus, further outward expansion of cages 12A and 12B via wedge 18 can cease and toggle joint 16 can takeover.

FIG. 8C is a side cross-sectional view of interbody implant 10 of FIG. 2 in the expanded state. Engagement of wedge 18 with stop surfaces 142A and 142B can initiate operation of toggle joint 16. As drive shaft 30 continues to be rotated by a driver instrument, wedge 18 can pull pin 24 closer to wedge 18. Furthermore, wedge 18 advances closer to the end (to the right in FIG. 8C) of first shaft 110 as second shaft 112 is pulled further inside of first shaft 110 due to the compound threading action mentioned above. Thus, toggle joint 16 can take over from wedge 18 in providing pivoting action to cages 12A and 12B. Toggle joint 16 can be more readily expanded after the initial expansion provided by wedge 18 to take advantage of the greater height of toggle joint 16. Specifically, linkages 22A and 22B when rotated away from each other on pin 24 are taller than wedge 18. Described another way, it can be more difficult to expand toggle joint 16 from the collapsed state when under load from anatomy due to the enhanced force being applied to linkages 22A and 22B due to lever effects of the anatomy. Thus, wedge 18 and toggle joint 16 work cooperatively and sequentially to take advantage of the mechanical benefits of each expansion mechanism.

Figure 9:
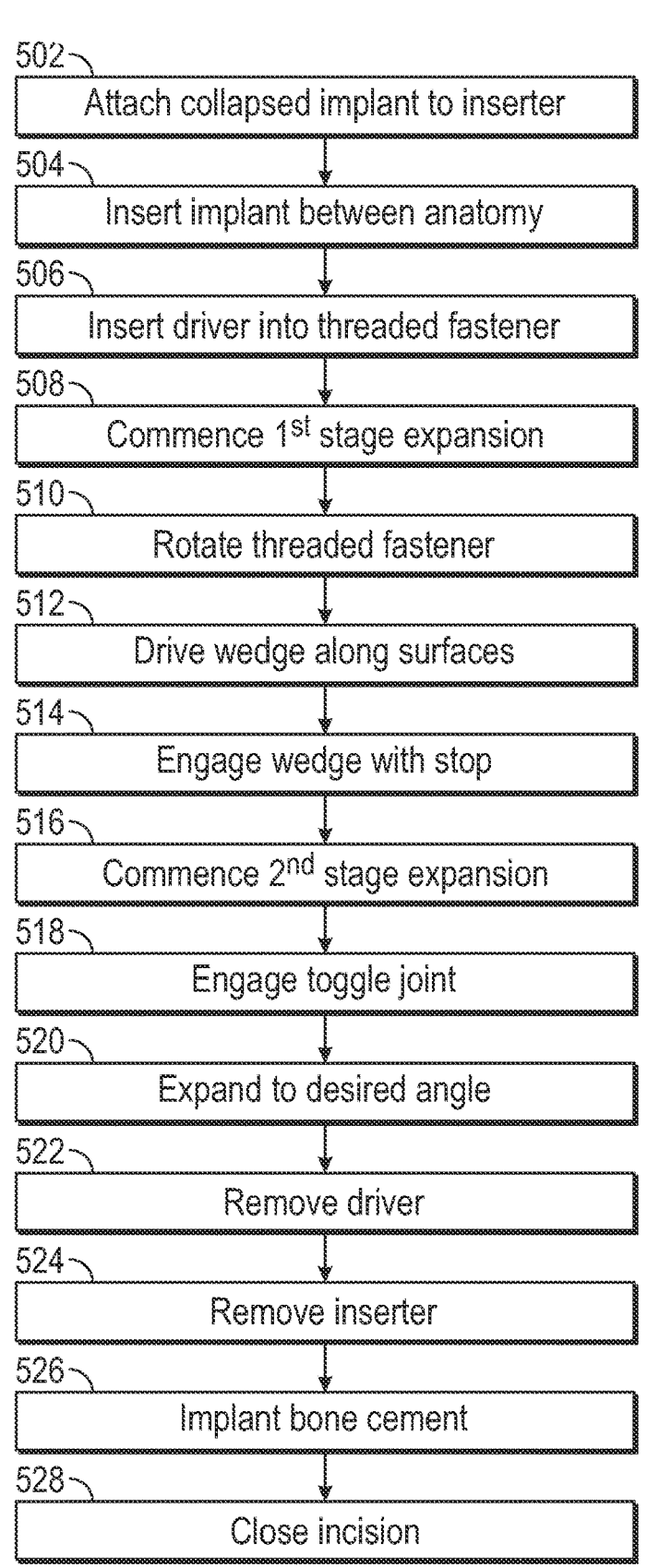
FIG. 9 is a line diagram illustrating a method of implanting a dual-action expandable intravertebral implant.

FIG. 9 is a line diagram illustrating method 500 of implanting dual-action expandable intravertebral implant 10. Interbody implant 10 can be implanted between adjacent bones, such as adjacent vertebrae, to promote bone ingrowth. A method of implanting interbody implant 10 can include properly preparing and performing an incision in a patient to access a medial, lateral or posterior portion of a spine adjacent an area where damaged or diseased intervertebral tissue is located. Soft tissue can be retracted using appropriate instrumentation to provide better access to the damaged or diseased intervertebral tissue. The damaged or diseased intervertebral tissue can be removed using appropriate methods to clear access to inferior and superior bone surfaces of the adjacent vertebrae.

At step 502, expandable intervertebral implant 10 can be attached to an inserter (e.g., inserter 600 of FIG. 10) in a collapsed state so as to minimize the height of intervertebral implant 10. The inserter can be attached to couplers 68A-70B.

At step 504, the inserter can be used to insert intervertebral implant 10 into the incision and between adjacent vertebrae, where damaged or diseased tissue has been removed. For example, an elongate inserter can be coupled to couplers 68A-70B to push implant 20 through the incision and to the target location. The inserter can be used to position implant 10 into the desired implant position. In other examples, interbody implant 10 can be attached to a tool, such as by threading a shaft of an insertion instrument into engagement with interbody implant 10. Interbody implant 10 can be manipulated by a surgeon, robot or another person to position insertion portion 36 in the incision.

Interbody implant 10 can be oriented in a desired direction such that insertion portion 36 is pointed toward the anterior of the spine and coupling portion 38 is pointed toward the posterior of the spine, for example. Crosspieces 94A and 94B can be engaged with soft tissue that is located medially or laterally of the implantation site in the spine. The insertion tool can be pushed to slide soft tissue across legs 50A-52B. The curvature of crosspieces 94A and 94B can push the soft tissue out of the way of interbody implant 10 to inhibit soft tissue from scraping along scallops 62A and 62B. The insertion tool can be pushed until legs 50A-52B engage the exposed superior and inferior bone surfaces of the adjacent vertebrae where disc material has been removed.

Legs 50A-52B can be pushed in between the adjacent vertebrae and can act as a wedge to initially spread the vertebrae to receive the full thickness of interbody implant 10 after expansion as described below with respect to steps 506-520. Interbody implant 10 can continue to be pushed until scallops 62A and 62B are positioned adjacent the exposed superior and inferior bone surfaces of the adjacent vertebrae. Scallops 62A and 62B can help engage with bone when implant 10 is finally positioned to prevent displacement by digging into boney structure. Interbody implant 10 can be positioned so as to be centered in the anterior-posterior direction on the vertebrae. If deemed desirable by the surgeon to verify placement of interbody implant 10, a surgeon can obtain imaging of the patient so that the location of implant 10 relative to the medial and lateral sides of the vertebrae can be viewed and measured.

At step 506, a driver can be extended into intervertebral implant 10, such as by being passed into and through the inserter.

As step 508, first stage expansion of intervertebral implant 10 can be commenced with implant 10 in the desired location.

At step 510, the driver can be inserted into drive shaft 30 to activate the first stage expansion. The driver can be engaged with drive socket 130 to rotate interior passage 126 and threaded exterior 134 relative to each other. Likewise, wedge 18 and shaft 124 can be rotated relative to each other.

At step 512, wedge 18 can be slid along angled surfaces 140A and 140B to push superior cage 12A and inferior cage 12B away from each other.

At step 514, wedge 18 can be configured to be advanced to engage stop surfaces 142A and 142B. Thus, wedge 18 can be prevented from further providing direct outward expansion of superior cage 12A and inferior cage 12B.

At step 516, the driver can continue to rotate drive shaft 30 to activate the second stage expansion. Stop surfaces 142A and 142B can be configured to allow wedge 18 facilitate operation of toggle joint 16.

At step 518, toggle joint 16 can be engaged by drive shaft 30 being pulled through wedge 18 to draw pin 24 closer to wedge 18, thereby causing linkages 22A And 22B to rotate at pin 24 to cause outward expansion of cages 12A and 12B proximate insertion portion 36, lifting cages 12A and 12B outward away from wedge 18.

At step 520, implant 10 can be expanded to the desired angle. In particular, angle α can be adjusted to meet the needs of a specific patient, such as a particular lordosis angle based on the level of the spine that implant 10 is inserted into.

At step 522, the driver for drive shaft 30 can be detached from implant 10 and withdrawn from the anatomy.

At step 524, the inserter can be detached from implant 10 and withdrawn from the anatomy.

At step 526, bone cement or bone graft material can be positioned within implant 10. For example, bone-growth-promoting material can be packed into windows 60A and 60B. In various examples, bone-growth-promoting material can be packed into windows 60A and 60B before implantation. However, in some embodiments described herein, bone-growth-promoting material can be packed after implantation. In other examples, bone graft material can be inserted into implant 10 before step 524.

At step 528, the incision in the patient can be appropriately closed to leave interbody implant 10 within the patient to allow implant 10 to fuse the adjacent vertebrae through, via, bone in-growth. With interbody implant 10 positioned between bone surfaces of the adjacent vertebrae, bone from the vertebrae can grow into the windows 60A and 60B to interact with the bone graft material placed therein. The bone-growth-promoting material located within windows 60A and 60B can interact with the vertebrae to enhance bone growth. Furthermore, movement of the vertebrae, such as by bending and twisting of the spine, can apply compression to interbody implant 10. Compressive forces applied to interbody implant 10 in the superior-inferior direction by the spine can be transmitted the bone-growth-promoting material to thereby stimulate biological growth of bone at the vertebrae contacting interbody implant 10. As bone grows into interbody implant 10, the superior and inferior vertebrae can become fused together through interbody implant 10.

Interbody implant 10 of the present disclosure can be configured for use in various spinal correction procedures. Intervertebral implants of the present disclosure can be used with different insertion approaches and for various levels of the spine. Specifically, the illustrated example can be used as a Transformational Lumbar Interbody Fusion (TLIF) device or a Posterior Lumbar Interbody Fusion (PLIF) device. However, the features and benefits of the present disclosure can additionally be configured for use as an anatomic Anterior Cervical Interbody Fusion (ACIF) device or a lordotic Anterior Cervical Interbody Fusion (ACIF) device.

TLIF devices can be configured for insertion in between vertebrae from a posterior side of the spinal column. More specifically, a TLIF device of the present disclosure can be configured for insertion into a spinal column between a spinous process and an adjacent transverse process. A TLIF device of the present disclosure can be configured, e.g., with different thicknesses, sizes, widths, lengths to accommodate usage at different levels in the spinal column or in different sized patients. A TLIF device of the present application can be rotated on a superior-inferior axis in a transverse plane while being inserted to the position TLIF device to extend across the spinal column. An insertion device can be coupled to coupling portion 38 and insertion portion 36 can be pushed through tissue into the spinal column such that superior and inferior surfaces 40 and 42 align with an inferior surface of a superior vertebra and a superior surface of an inferior vertebra.

PLIF devices can be configured for insertion in between vertebrae from a posterior side of the spinal column. More specifically, a PLIF device of the present disclosure can be configured for insertion into a spinal column between a spinous process and an adjacent transverse process. A PLIF device of the present disclosure can be configured, e.g., with different thicknesses, sizes, widths, lengths to accommodate usage at different levels in the spinal column or in different sized patients. A PLIF device of the present disclosure can inserted straight into the spinal column on one side of the spinal cord. In examples, a second PLIF device can be inserted straight into the spinal column on the opposite side of the spinal column. An insertion device can be coupled to coupling portion 38 and insertion portion 36 can be pushed through tissue into the spinal column such that superior and inferior surfaces 40 and 42 align with an inferior surface of a superior vertebra and a superior surface of an inferior vertebra.

The systems, devices and methods discussed in the present application can be useful in implanting expandable interbody implants, such as those that can be used in spinal correction procedures involving lateral, transverse, anterior or posterior insertion of a spacer between adjacent vertebrae. The interbody implant can have first and second bodies that can be coupled to each other at a pivoting coupling. The angle between the first and second bodies can be adjusted to push adjacent anatomy into a desired orientation, such as a desired angle therebetween. The first and second bodies can be moved into the desired angle using two expansion mechanisms that can provide different actuation qualities, such as expansion strength or force, expansion height and mechanical leverage. Thus, the two expansion mechanisms can be arranged in conjunction with an actuation mechanism to sequentially operate to pivot the first and second bodies relative to each other to overcome resistance from the anatomy and position the anatomy in the desired orientation. The first expansion mechanism can be configured to overcome high initial loading on the implant from the anatomy. The second expansion mechanism can be configured to provide increased expansion beyond the configuration of the first expansion mechanism when initial loading from the anatomy is overcome.

Figure 10:
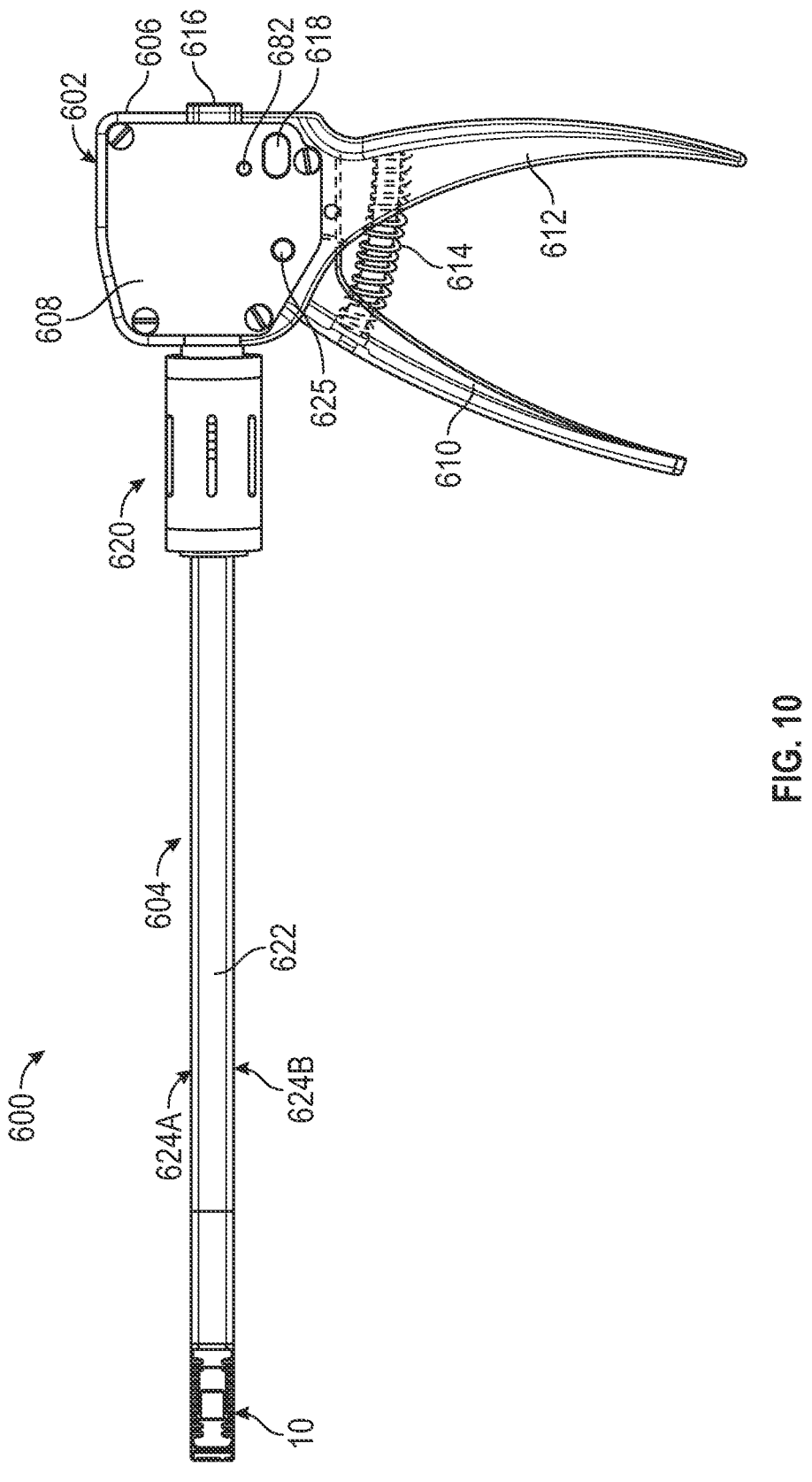
FIG. 10 is a side view of an inserter comprising a handle and an insertion rod coupled to an interbody implant of the present disclosure.

FIG. 10 is a side view of inserter 600 comprising handle 602 and insertion rod 604 coupled to interbody implant 10 of the present disclosure. Handle 602 can comprise body 606, cover 608, trigger 610, handpiece 612, spring 614, access port 616 and lock button 618. Insertion rod 604 can comprise coupling controller 620, shaft 622 and first coupling arm 624A.

Body 606 can comprising a housing be used to hold a mechanism (e.g., push mechanism 652 of FIG. 12A) for moving a pushrod (e.g., pushrod 630 of FIG. 11A or pushrod 631 of FIG. 11B) through inserter 600 to dispense a material into implant 10. Coupling controller 620 can be operated to couple and uncouple implant 10 to the distal end of shaft 622. Trigger 610 can be pivotably coupled to body 606 and cover 608 at pin 625. Handle 602 and trigger 610 can be configured to be held by a user to dispense a surgical material, such as a material that promotes bone growth, an artificial bone graft material or a natural bone graft material. Squeezing of trigger 610 toward handle 602 can cause movement of a piston in shaft 622 to push material out of a cartridge (e.g., cartridge 656 of FIG. 12) loaded into shaft 622 and into implant 10. Button 618 can be operated to change a rate at which material is dispensed from inserter 600 in combination with the use of different pushrods, as shown in FIGS. 11A and 11B.

Figure 11A:
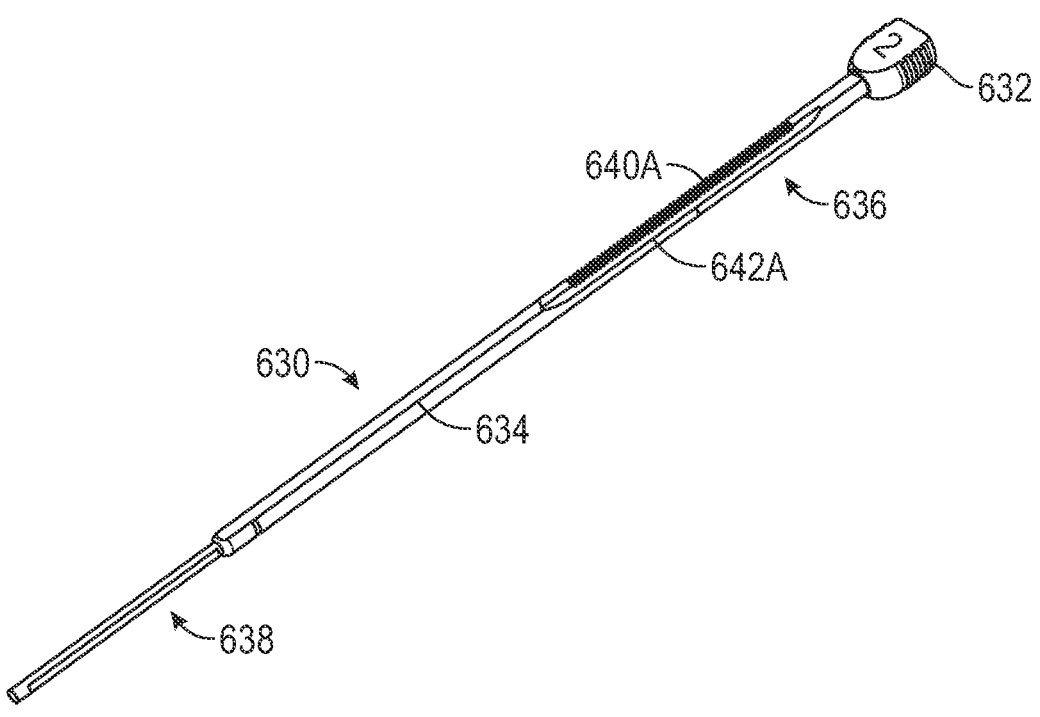
FIG. 11A is a perspective view of a pushrod configured for use with the inserter of FIG. 10 for high volume dispensing.

FIG. 11A is a perspective view of pushrod 630 configured for use with inserter 600 of FIG. 10. Pushrod 630 can comprise knob 632 and shaft 634, which can comprise engagement portion 636 and piston portion 638. A top or superior side (as illustrated) of engagement portion 636 can comprise tooth track 640A and groove 642A. As can be seen in FIG. 18A, a bottom or inferior side of engagement portion 636 can comprise tooth track 640B and groove 642B. As is discussed with reference to FIGS. 17, 19A and 19B, pushrod 630 can be configured to interact with push mechanism 652 (FIG. 12) in only one way to cause dispensing at a first rate. However, other pushrods can be configured to interact with push mechanism 652 in different ways to cause dispensing at different rates.

Figure 11B:
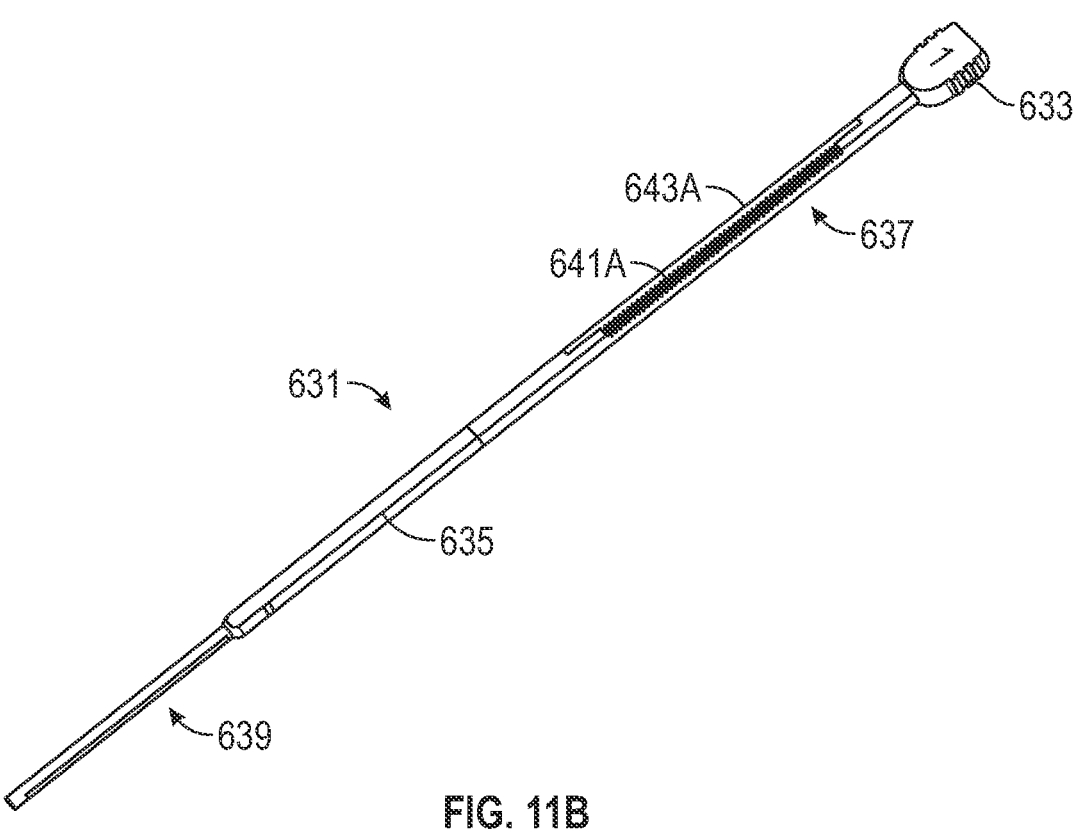
FIG. 11B is a perspective view of a pushrod configured for use with the inserter of FIG. 10 for low volume dispensing.

FIG. 11B is a perspective view of pushrod 631 configured for use with inserter 600 of FIG. 10. Pushrod 631 can comprise knob 633 and shaft 635, which can comprise engagement portion 637 and piston portion 639. A top or superior side (as illustrated) of engagement portion 637 can comprise tooth track 641A and groove 643A. As can be seen in FIG. 18B, a bottom or inferior side of engagement portion 637 can comprise tooth track 641B and groove 643B. As is discussed with reference to FIGS. 17, 19A and 19B, pushrod 631 can be configured to interact with push mechanism 652 (FIG. 12A) in only one way to cause dispensing at a second rate that is different than the first rate.

Figures 12A, 12B:
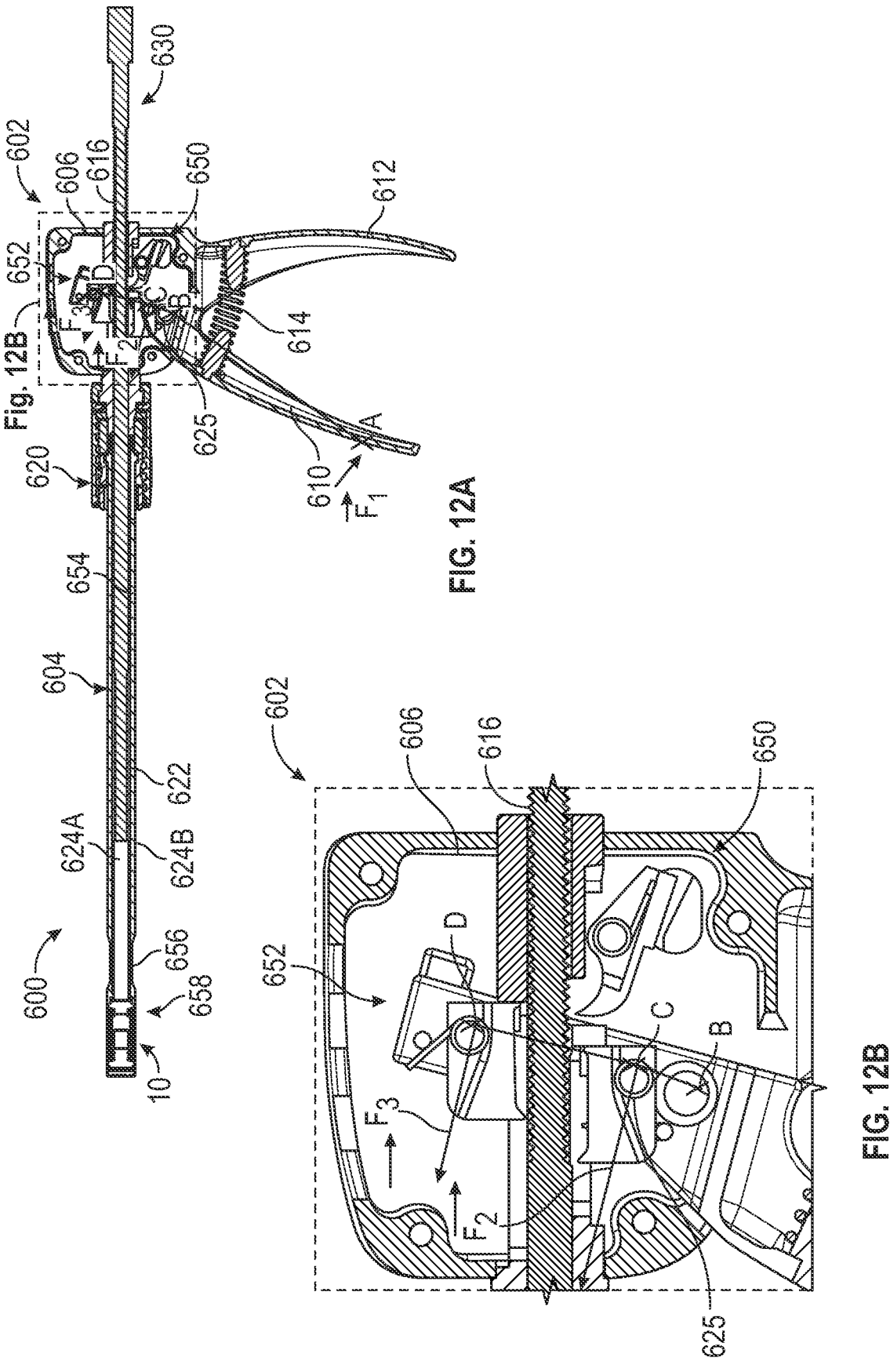
FIG. 12A is a cross-sectional view of the inserter of FIG. 10 with the high-volume pushrod inserted therethrough.
FIG. 12B is a close-up view of first and second pawls acting on the pushrod of FIG. 12A illustrating a force diagram.

FIG. 12A is a cross-sectional view of inserter 600 of FIG. 10 with pushrod 630 inserted therethrough. Inserter 600 can comprise locking mechanism 650, push mechanism 652 and coupling controller 620. Shaft 622 of insertion rod 604 can comprise internal lumen 654 through which pushrod 630 can extend and in which cartridge 656 can be positioned. Distal end 658 of insertion rod 604 can couple to implant 10. A proximal portion of insertion rod 604 can be connected to access port 616.

Access port 616 can be aligned with lumen 654 to allow passage of pushrod 630 from a proximal side of body 606 through to implant 10. Trigger 610 can be used to actuate push mechanism 652 to advance pushrod 630 into lumen 654 in a controlled manner and with a requisite level of force to expel material from cartridge 656. Spring 614 can be used to bias trigger 610 away from handle 612. As discussed in greater detail below, different pushrods can be loaded into push mechanism 652 to cause advancement by push mechanism 652 at different rates. Locking mechanism 650 can be used to selectively prevent movement of pushrod 630. Coupling controller 620 can facilitate coupling and coupling of implant 10 from insertion rod 604 from a proximal end of shaft 622. As discussed in greater detail below, rotation of coupling controller 620 can cause deflection of coupling arm 624A and coupling arm 624B (FIG. 20B) to facilitate coupling and uncoupling of implant 10.

FIG. 12B is a close-up view of first and second pawls 672A and 672B acting on pushrod 630 of FIG. 12A. FIG. 12B illustrates forces F2 and F3 acting on pushrod 630, which are discussed in greater detail below.

Figure 13:
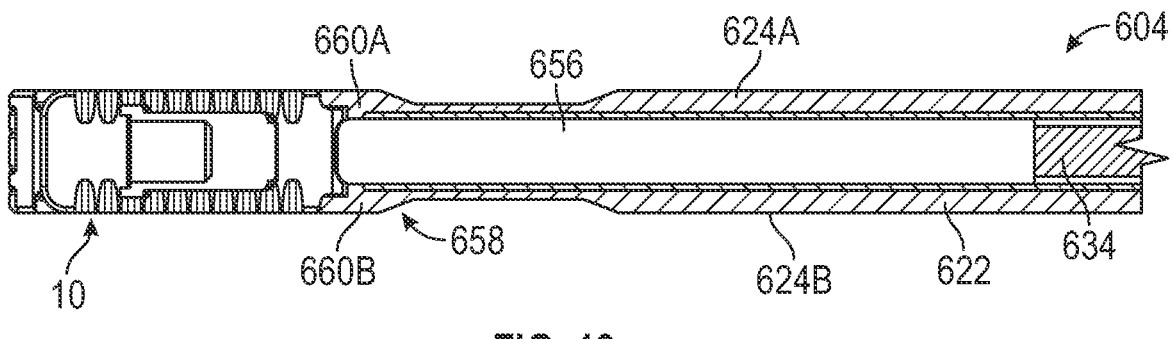
FIG. 13 is a close-up view of the insertion rod of the inserter of FIG. 12A showing the interbody implant coupled thereto and a surgical material cartridge positioned therein.

FIG. 13 is a close-up view of insertion rod 604 of inserter 600 of FIG. 12A showing interbody implant 10 and bone graft material cartridge 656. Cartridge 656 can be loaded into distal end 658 of shaft 622 after implant 10 has been inserted into the anatomy and adjusted (e.g., expanded) to the desired configuration. Shaft 622 should be empty to allow for insertion of a tool (e.g., screwdriver) to expand implant 10. Cartridge 656 can be filled with bone graft material and can be clipped to the tip of a pushrod (e.g., pushrod 630). The assembly of cartridge 656 and pushrod 630 can be inserted by access port 616 after step 520 of FIG. 9. Shaft 622 can include pads 660A and 660B to center cartridge 656 within lumen 654 and prevent cartridge 656 from passing out of lumen 654. (See FIG. 20B.) Pads 660A and 660B can be located can be located near distal end 658 in order to position cartridge 656 proximate implant 10. As such, advancement of shaft 634 via push mechanism 652 into cartridge 656 can cause bone graft material to enter implant 10 such as through portals 64A and 64B (FIG. 1).

Figure 14:
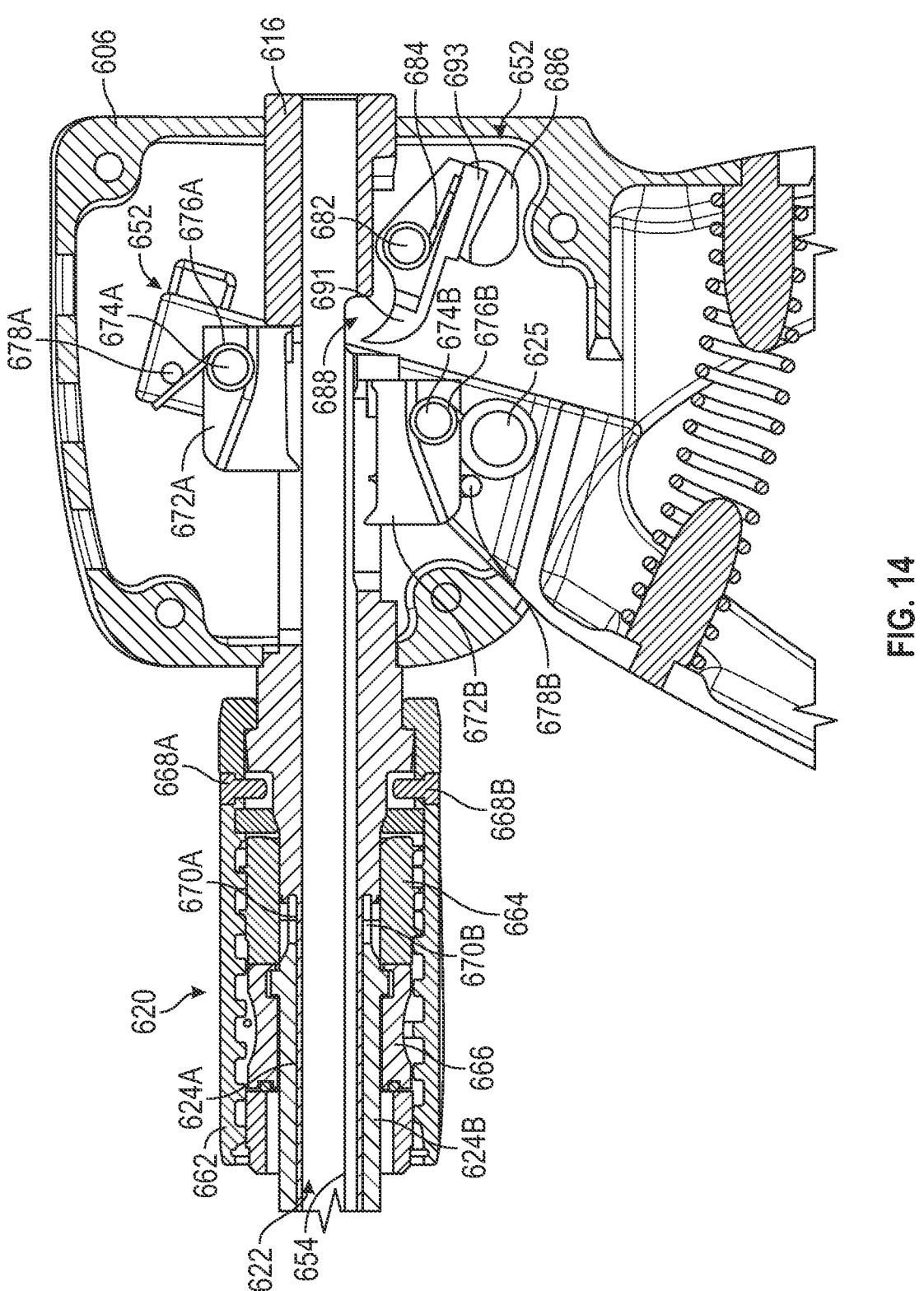
FIG. 14 is a close-up view of the handle of the inserter of FIG. 12A showing a coupling controller, a push mechanism and a locking mechanism.
Figure 15:
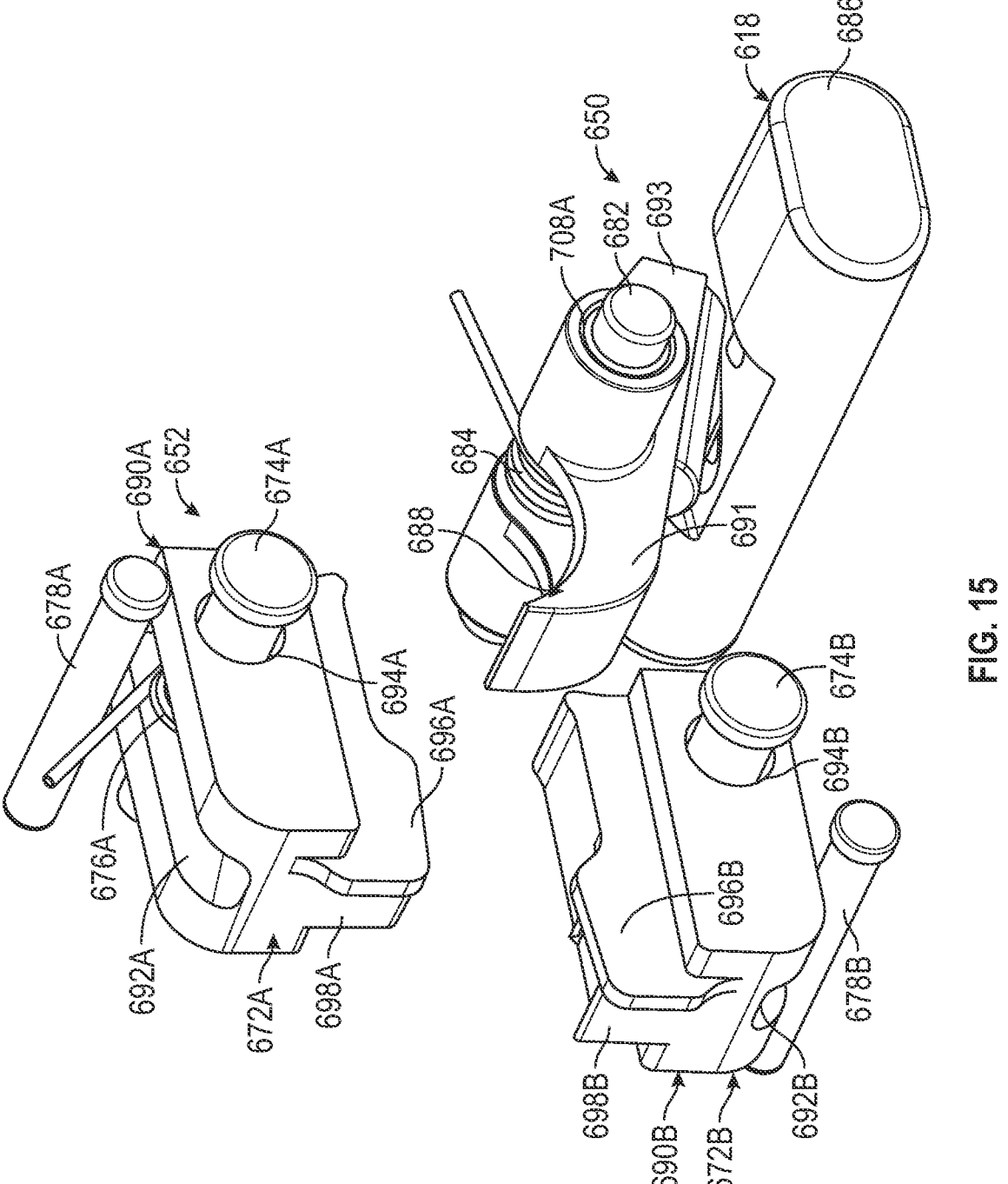
FIG. 15 is a perspective view of the push mechanism and the locking mechanism of FIG. 14 shown in isolation.

FIG. 14 is a close-up view of body 606 of inserter 600 of FIG. 12A showing coupling controller 620, push mechanism 652 and locking mechanism 650. FIG. 15 is a perspective view of push mechanism 620 and locking mechanism 650 of FIG. 14 shown in isolation. FIGS. 14 and 15 are discussed concurrently.

Coupling controller 620 can comprise knob 662, piston 664, cover 666 and pins 668A and 668B. Shaft 622 can comprise first channel 670A and second channel 670B into which coupling arms 624A and 624B can be positioned, respectively.

Push mechanism 652 can comprise first pawl 672A, second pawl 672B, first pivot pin 674A, second pivot pin 674B, first biasing element 676A, second biasing element 676B, first bias pin 678A and second bias pin 678B.

Locking mechanism 650 can comprise pin 682, biasing element 684, button 618 and locking pawl 688. Locking pawl 688 can further comprise tang 691 and latch 693.

As shown in FIG. 15, first pawl 672A can comprise first body 690A comprising groove 692A, pin bore 694A, rail 696A and prong 698A; and second pawl 672B can comprise second body 690B comprising groove 692B, pin bore 694B, rail 696B and prong 698B.

Operation of locking mechanism 650 is described with reference to FIGS. 16A and 16B. Operation of push mechanism 652 is described with reference to FIGS. 17-19B. Operation of coupling controller 620 is described with reference to FIGS. 20A-25.

Figure 16A:
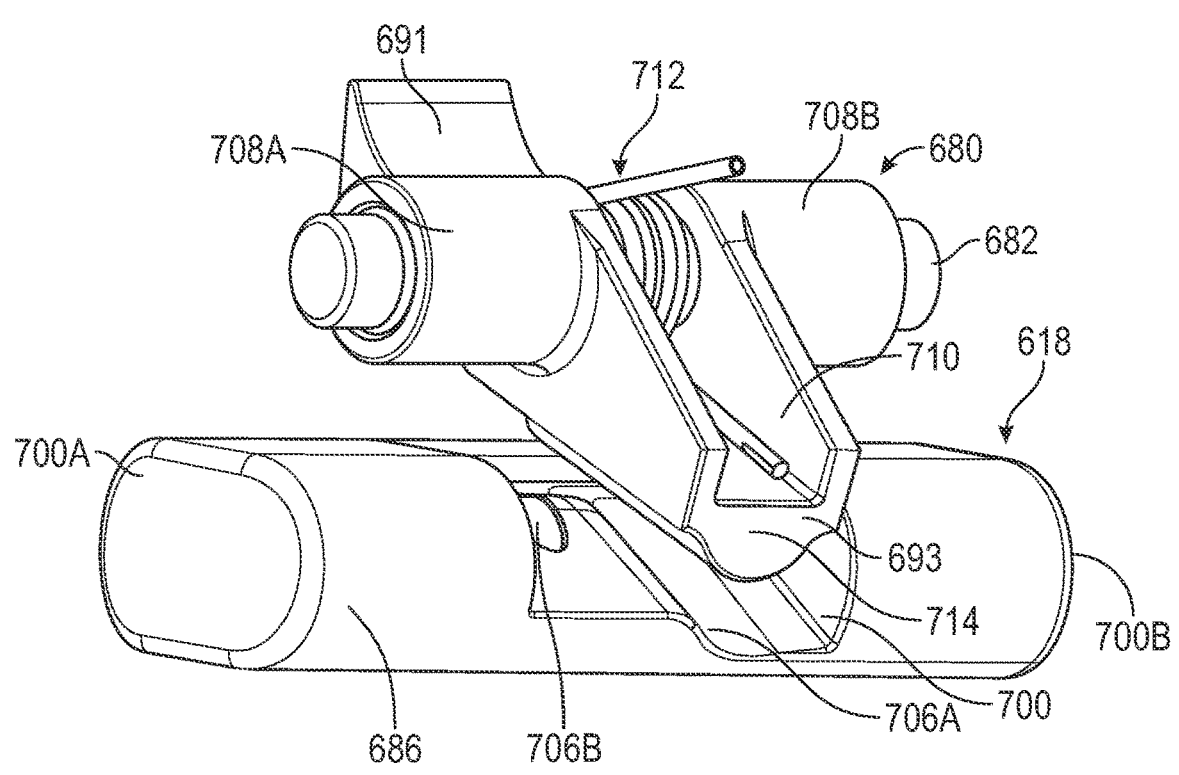
FIG. 16A is a perspective view of the locking mechanism of FIG. 15 showing a locking pawl and a button.
Figure 16B:
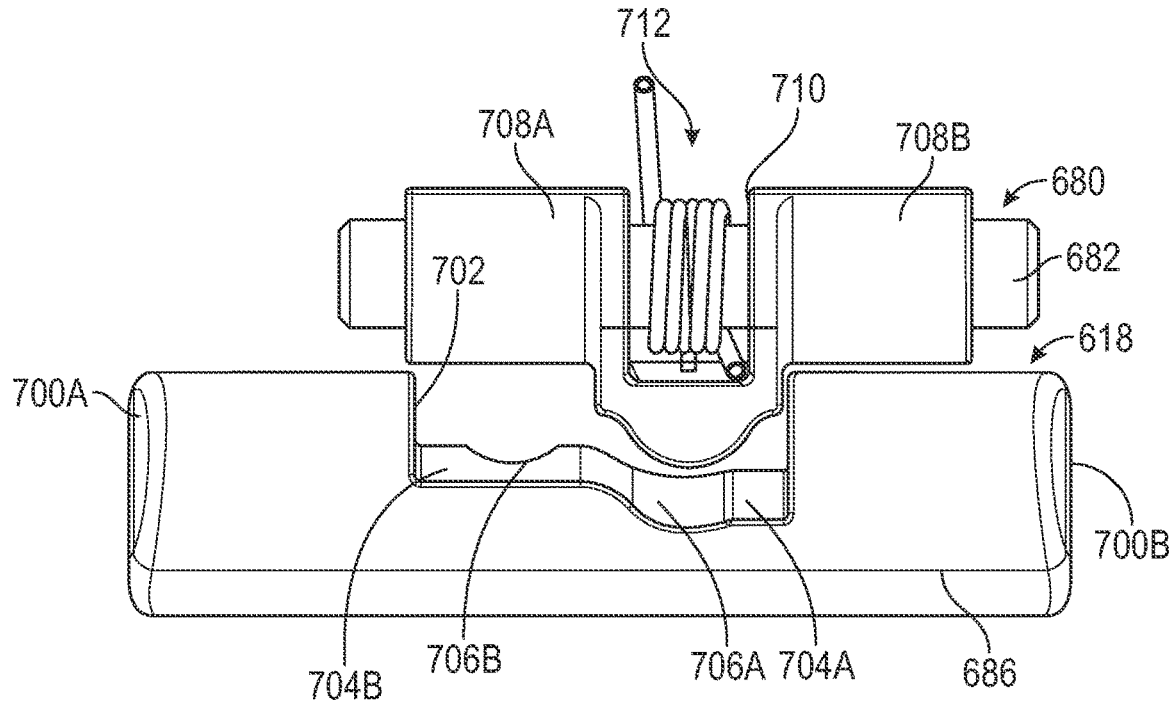
FIG. 16B is a rear view of the locking mechanism of FIG. 15 showing the locking pawl selectively engageable with the button.

FIG. 16A is a perspective view of locking mechanism 650 of FIG. 15 showing locking pawl 680 positioned relative to button 618. FIG. 16B is a rear view of locking mechanism 650 of FIG. 15. FIGS. 16A and 16B are discussed concurrently.

Button 618 can comprise body 686 comprising first and second pads 700A and 700B, and pawl window 702 comprising lock surface 704A with notch 706A and dispense surface 704B with notch 706B.

Body 686 can be positioned in body 606 (FIG. 10) such that pads 700A and 700B extend through corresponding sockets in body 606 and cover 608. As such, button 618 can be accessible on the exterior of body 606 to a user of inserter 600. Body 686 can fit into the corresponding sockets via an interference fit that allows sliding. Body 686 can be prevented from separating from body 606 via the presence of locking pawl 680.

Locking pawl 680 can be mounted to body 606 via pin 682, which can be fit into corresponding bores in body 606 and cover 608. Locking pawl 680 can comprise cylinder portions 708A and 708B that can include sockets for receiving pin 682. Slot 710 can be positioned between cylinder portions 708A and 708B to allow for the presence of biasing device 712. Biasing device 712 can comprise a torsion spring having a wire wound into a coil that can be disposed on pin 682 and ends of the wire extended therefrom. Locking pawl 688 can further comprise tang 691 and latch 693. As such, one arm of biasing device 712 can press against a component of inserter 600 (e.g., see access port 616 of FIG. 14) and another arm of biasing device 712 can press against latch 693. Thus, latch 693 can be biased into pawl window 702 against one of lock surface 704A and dispense surface 704B, depending on the position of body 686. Bulge 714 of latch 693 can seat into one of notches 706A and 706B to inhibit lateral translation of button 618. Lock surface 704A can be further below pin 682 than dispense surface 704B, which allows tang 691 to be positioned higher when latch 693 is engaged with lock surface 704A as compared to dispense surface 704B, to engage pushrod 630 (FIG. 12A) to prevent movement of pushrod 630. As described below, pushrod 630 can comprise teeth that receive tang 691. Dispense surface 704B can be closer to pin 682 than lock surface 704A, which allows tang 691 to be positioned lower when latch 693 is engaged with dispense surface 704B as compared to lock surface 704A, to disengage pushrod 630 (FIG. 12A) and allow pushrod 630 to move.

Figure 17:
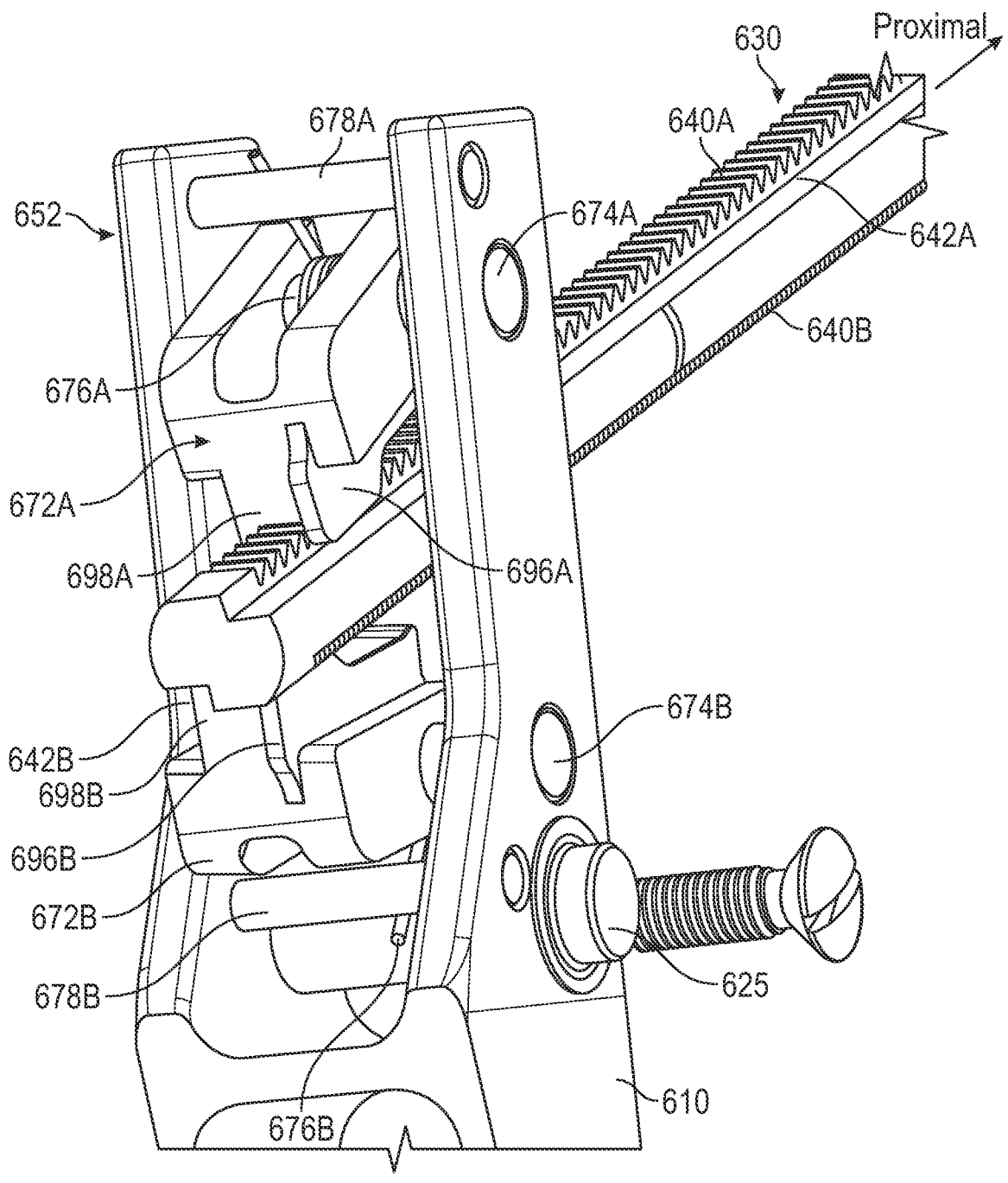
FIG. 17 is a perspective view of the push mechanism of FIG. 15 engaged with a pushrod.
Figures 18A, 18B:
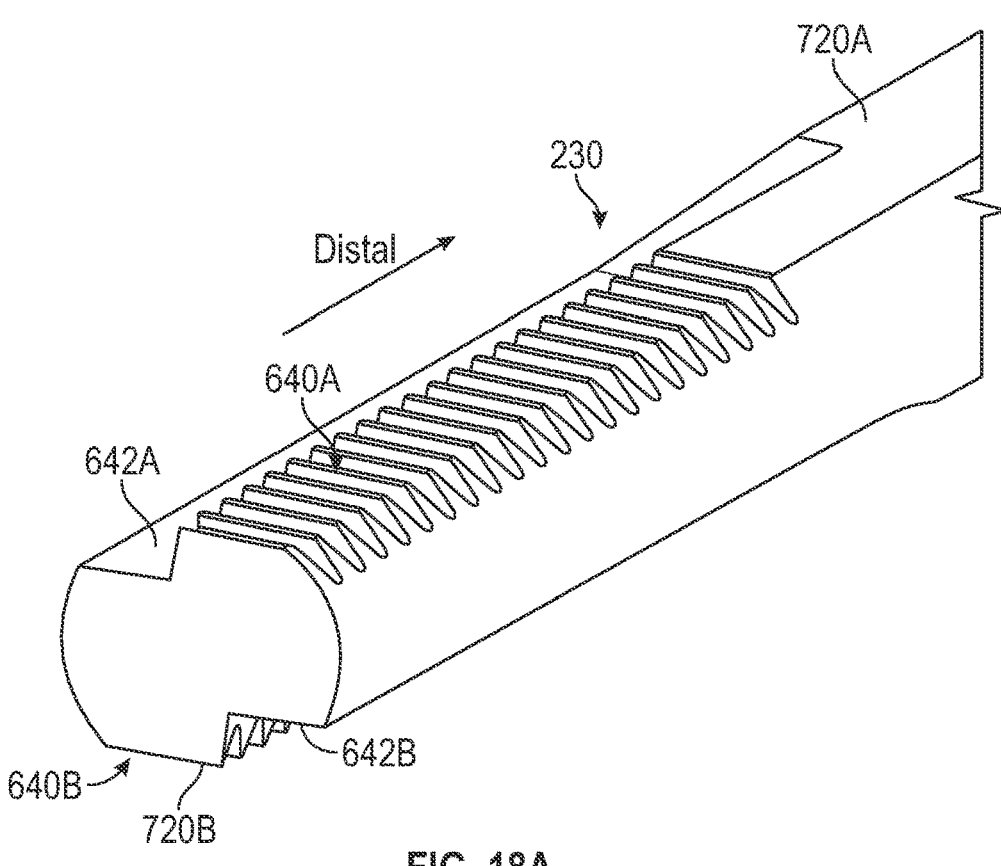
FIG. 18A is a rear perspective view of a high-volume pushrod shown from a proximal-to-distal viewpoint to illustrate opposing tracks of teeth.
FIG. 18B is a rear perspective view of a low-volume pushrod shown from a proximal-to-distal viewpoint to illustrate opposing tracks of teeth.
Figures 19A, 19B:
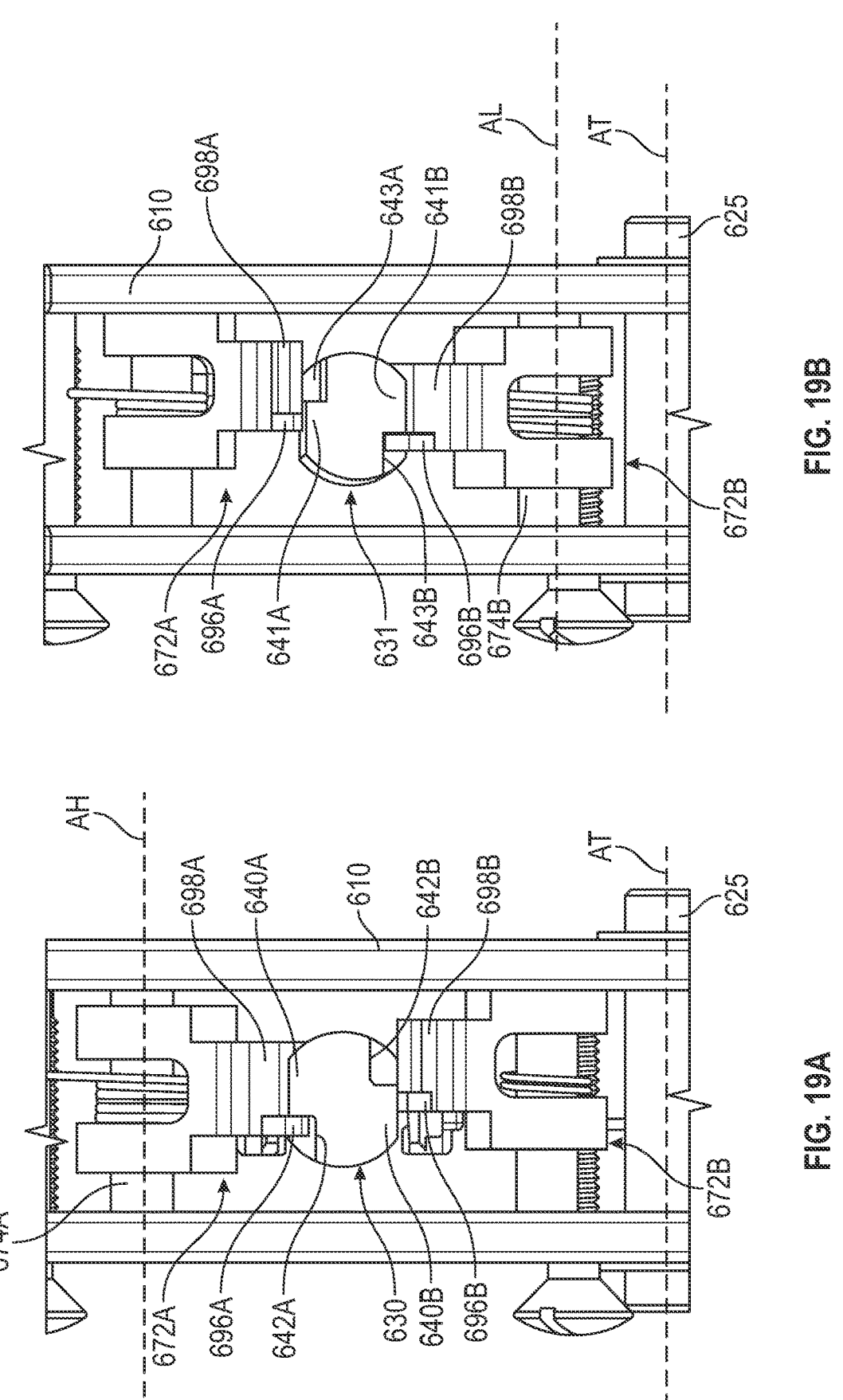
FIG. 19A is a rear cross-sectional view of the high-volume pushrod of FIG. 18A loaded into the push mechanism.
FIG. 19B is a rear cross-sectional view of the low-volume pushrod of FIG. 18B loaded into the push mechanism.

FIG. 17 is a perspective view of push mechanism 652 of FIG. 15 engaged with pushrod 630. First pawl 672A can be mounted to trigger 610 via pin 674A and second pawl 672B can be mounted to trigger 610 via pin 674B. Pawls 672A and 672B can be rotatably mounted to pawl pins 674A and 674B. Pins 678A and 678B can be mounted to trigger 610 outward of pins 674A and 674B relative to pushrod 630. Biasing elements 676A and 676B can be mounted to pins 678A and 678B to bias first and second pawls 672A and 672B inward toward pushrod 630, respectively. Biasing elements 676A and 676B can comprise torsion springs having wires wound into coils that can be disposed on pins 678A and 678B and ends of the wires extended therefrom. Thus, both of pawls 672A and 672B will contact pushrod 630, but only one will functionally engage pushrod 630 depending on the configuration of pushrod 630 and other pushrods. Specifically, both of rails 696A and 696B and prongs 698A and 698B will be biased toward pushrod 630, but only one of rails 696A and 696B from one of pawls 672A and 672B and one of prongs 698A and 698B from the other of pawls 672A and 672B engage the pushrod. As shown in FIGS. 19A and 19B, one of rails 696A and 696B will engage one of grooves 642A and 642B to allow engagement of one of prongs 698A and 698B with one of teeth 640A and 640B to allow movement of pushrod 230, while the other of rails 696A and 669B will engage the other of teeth 640A and 640B to prevent engagement of the other of prongs 698A and 698B with the other of teeth 640A and 640B to prevent movement of pushrod 230.

FIG. 18A is a rear perspective view of high-volume pushrod 230 of FIG. 17 showing opposing tracks of teeth 640A and 640B adjacent channels 642A and 642B. Pushrod 230 can have a circular cross-sectional profile with first surface 720A and second surface 720B forming flats extending along the length of pushrod 230. First surface 720A and second surface 720B can comprise surfaces into which teeth 640A and 640B and channels 642A and 642B can be formed, respectively.

Channels 642A and 642B are located on opposing diagonal corners of pushrod 230. Likewise, teeth 640A and 640B are located on opposing diagonal corners of pushrod 230. As such, whether first surface 720A is oriented upward (superior) or second surface 720B is oriented upward (superior), the top of pushrod 230 will always have either teeth 640A or 640B on the right (as shown in FIG. 18A) and either channels 642A and 642B on the left (as shown in FIG. 18A). Thus, as can be seen in FIG. 18A, the upward facing teeth will always engage with prong 698A and the upward facing channel will always receive rail 696A (without contact between rail 696A and the channel). Conversely, as can be seen in FIG. 18A, the downward facing teeth will always engage with rail 696B and the downward facing channel will always face prong 698B (without contact between prong 696B and the teeth). Thus, only first pawl 672A will engage with pushrod 230 as configured in the illustration of FIG. 18A.

FIG. 18B is a rear perspective view of low-volume pushrod 231 configured to engage a different portion of the push mechanism 652 than high-volume pushrod 230. Low-volume pushrod 231 can comprise opposing tracks of teeth 641A and 641B adjacent channels 643A and 643B. Pushrod 231 can have a circular cross-sectional profile with first surface 721A and second surface 721B forming flats extending along the length of pushrod 231. First surface 721A and second surface 721B can comprise surfaces into which teeth 641A and 641B and channels 643A and 643B can be formed, respectively.

Channels 643A and 643B are located on opposing diagonal corners of pushrod 231. Likewise, teeth 641A and 641B are located on opposing diagonal corners of pushrod 231. As such, whether first surface 721A is oriented upward (superior) or second surface 721B is oriented upward (superior), the top of pushrod 231 will always have either teeth 641A or 641B on the left (as shown in FIG. 18B) and either channels 643A and 643B on the right (as shown in FIG. 18B). Thus, as can be seen in FIG. 18B, the downward facing teeth will always engage with prong 698B and the downward facing channel will always receive rail 696B (without contact between rail 696B and the channel). Conversely, as can be seen in FIG. 18B, the upward facing teeth will always engage with rail 696A and the upward facing channel will always face prong 698A (without contact between prong 696A and the teeth). Thus, only second pawl 672B will engage with pushrod 231 as configured in the illustration of FIG. 18B.

FIG. 19A is a rear cross-sectional view of high-volume pushrod 230 of FIG. 18A loaded into push mechanism 652. FIG. 19B is a rear cross-sectional view of low-volume pushrod 231 of FIG. 18B loaded into push mechanism 652. Trigger 610 is configured to rotate about trigger axis AT of pin 625. As shown in FIG. 19A, pawl 672A is configured to rotate about high-speed axis AH of pin 674A. As shown in FIG. 19B, pawl 672B is configured to rotate about low-speed axis AL of pin 674B. High-speed axis AH is further away from trigger axis AT than low-speed axis AL. As such, rotation of trigger 610 can cause pawl 672A to be moved with a higher velocity and lower force than pawl 672B. Thus, pawl 672A can cause a push rod configured to engage with pawl 672A (e.g., pushrod 230) faster and with less force than pawl 672B can cause a pushrod configured to engage with pawl 672B (e.g., pushrod 231) to move. As shown in FIG. 12A, pawls 672A and 672B and trigger 610 can generate forces F1, F2 and F3 about pin 625, as summarized in Equations 1-4.

$$\vec{F_1} \times AB = \vec{F_2} \times BC = \vec{F_3} \times BD \qquad \text{Equation [1]}$$

$$AB > BD > BC \qquad \text{Equation [2]}$$

$$\vec{F_2} > \vec{F_3} > \vec{F_1} \qquad \text{Equation [3]}$$

$$\vec{V_A} > \vec{V_D} > \vec{V_C} \qquad \text{Equation [4]}$$

In examples, it can be advantageous to dispense substitute (e.g., artificial) bone graft material at an upper rate than natural bone graft material because artificial material can flow easier than biological bone graft material.

Figures 20A, 20B:
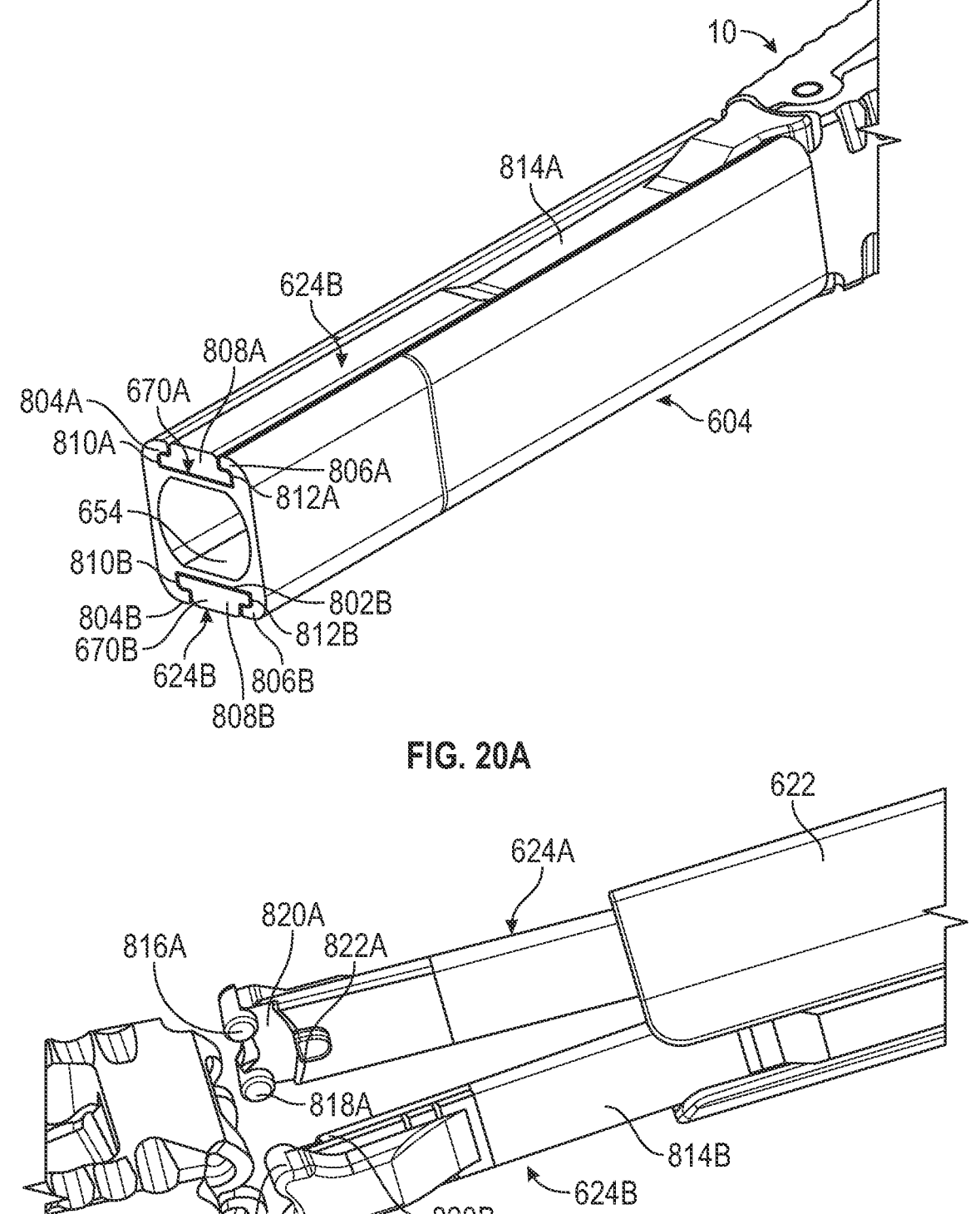
FIG. 20A is a rear perspective view of a distal portion of the insertion rod of FIG. 10 engaged with an interbody implant.
FIG. 20B is a front perspective view of a distal portion of the insertion rod of FIG. 10 disengaged from an interbody implant.

FIG. 20A is a rear perspective view of a distal portion of insertion rod 604 of FIG. 10 engaged with interbody implant 10. Insertion rod 604 can comprise central lumen 654, first channel 670A and second channel 670B. First coupling arm 624A can be disposed in first channel 670A and second coupling arm 624B can be disposed in second channel 670B. First channel 670A can comprise base 802A and overhanging flanges 804A and 806A. Second channel 670B can comprise base 802B and overhanging flanges 804B and 806B.

Figures 24, 25:
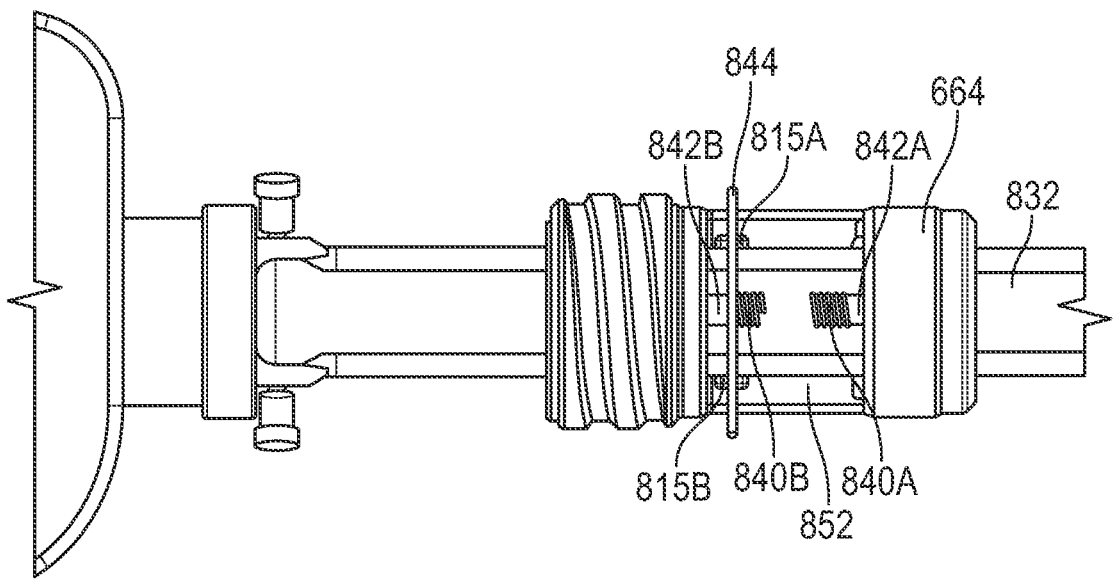
FIG. 24 is a side view of the coupling controller of FIG. 23 with an access cover removed from the translation cam.
FIG. 25 is side cross-sectional view of the coupling controller of FIG. 22 showing engagement of the control knob and the translation cam.

First coupling arm 624A can comprise body 808A and flanges 810A and 812A, thereby giving first coupling arm 624A a T-shaped cross-section. Second coupling arm 624B can comprise body 808B and flanges 810B and 812B, thereby giving second coupling arm 624B a T-shaped cross-section. However, first coupling arm 624A and second coupling arm 624B can additionally include flat regions 814A and 814B where body 808A and body 808B are tapered down to the height of flanges 810A-812B. Coupling arms 624A and 624B can comprise shanks that slide along bases 802A and 802B of channels 670A and 670B, respectively. As shown in FIG. 25, coupling arms 624A and 624B can include prongs 815A and 815B that engage with coupling controller 620 to produce distal and proximal movement of arms 624A and 624B.

Figure 21:
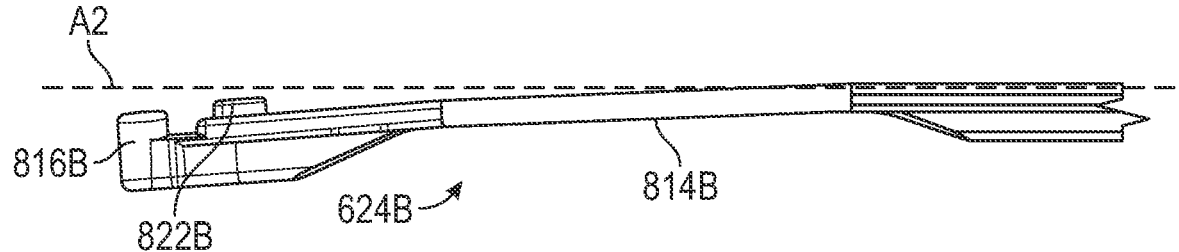
FIG. 21 is a side view of a coupling arm of the insertion rod of FIGS. 20A-20C showing curvature of the coupling arm.

When arms 624A and 624B are retracted proximally into channels 670A and 670B (such that distal coupling portions (e.g., couplers 816A-818B of FIG. 20B) are immediately proximate the distal end of shaft 622), bodies 808A and 808B extend generally parallel with channels 670A and 670B, as well as shaft 622 of insertion rod 604. However, as can be seen in FIG. 21, bodies 808A and 808B can have a curvature to bias the distal coupling portions away from shaft 622. Thus, when coupling controller 620 is operated to push arms 624A and 624B distally, the distal coupling portions can move away from each other to open up and receive or release implant 10, as shown in FIG. 20B. Flat regions 814A and 814B can comprised thinned down portions of arms 624A and 624B that have rectangular cross-sectional profiles to allow arms 624A and 624B a greater ability to flex.

FIG. 20B is a front perspective view of a distal portion of insertion rod 604 of FIG. 10 disengaged from interbody implant 10. First coupling arm 624A and second coupling arm 624B can be extended out from channels 670A and 670B to allow for separation of arms 624A and 624B from each other due to, for example, curvature arising from pre-bends in each of arms 624A and 624B.

First coupling arm 624A can include couplers 816A and 818A, groove 820A and pad 660A. Second coupling arm 624B can include couplers 816B and 818B, groove 820BA and pad 822B. Couplers 816A-818B can be sized to fit within couplers 68A-70B of implant 10 (See FIGS. 1 and 4). Couplers 68A-70B can comprise arcuate slots and couplers 816A-818B can comprise circular pads. The width of the arcuate slots can be slightly larger than the diameter of the circular pads to allow the pads to slide along an arcuate path with the slots. As such, implant 10 can be expanded and contracted while couplers 816A-818B remain engaged with couplers 68A-70B. Grooves 820A and 820B can be curved to mate with corresponding curvatures on implant 10 to provide a secure fit between arms 624A and 624B and implant 10.

Figure 20C:
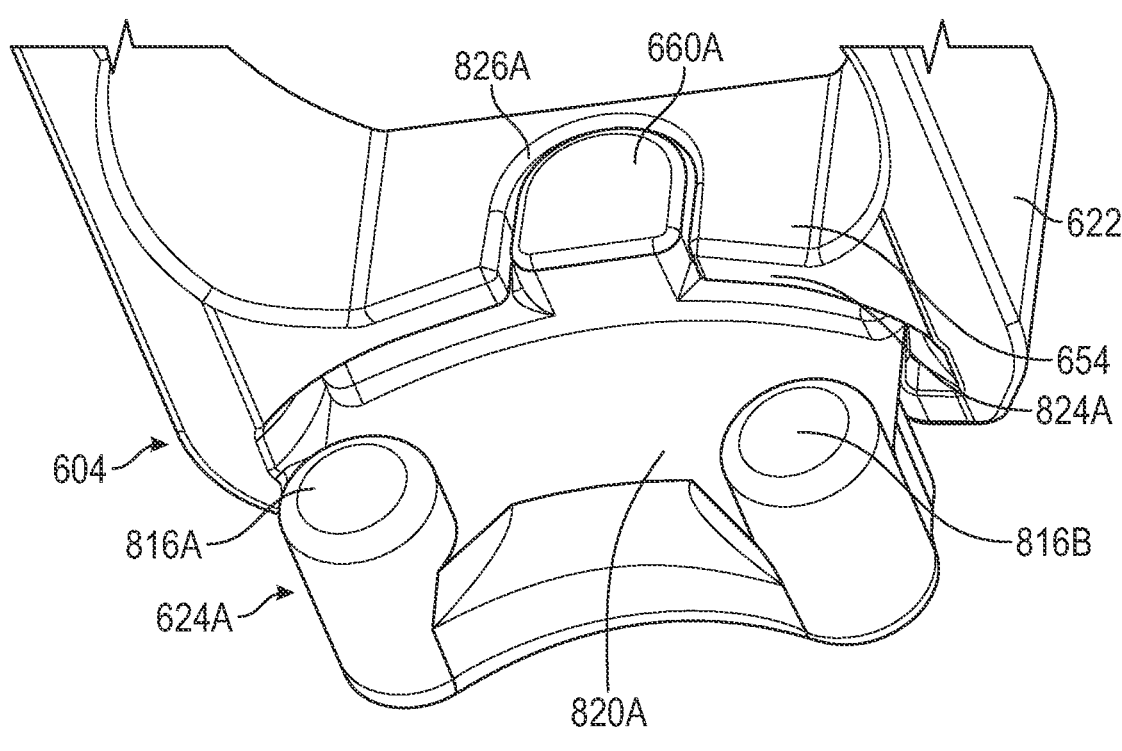
FIG. 20C is a distal end view of the insertion rod of FIG. 10 showing a coupling arm mated therewith.

FIG. 20C is a distal end view of insertion rod 604 having coupling arm 624A mated therewith. Coupling arm 624A can comprise couplers 816A and 818B, groove 820A and pad 660A. Coupling arm 624B can comprise corresponding components as coupling arm 624A shown in FIG. 20C. Insertion rod 604 can comprise shaft 622, internal lumen 654, implant cutout 824A and pad cutout 826A. Insertion rod 604 can additionally include a corresponding implant cutout opposing cutout 824A and a corresponding pad cutout opposing pad cutout 826A. Cutout 824A and the opposing cutout can correspond to the shape of grooves 820A and 820B to closely conform to the shape of implant 10. As mentioned, pad 660A and 660B (FIG. 13) can be used to engage cartridge 656.

FIG. 21 is a side view of coupling arm 624A of insertion rod 604 of FIGS. 20A-20C showing curvature of body 808A of coupling arm 624A. The majority of the length of arm 624A from prongs 815A (FIG. 25) to the portion shown in FIG. 21 can extend straight, parallel to shaft 622, along axis A2. However, the distal most portion of arm 624A can be curved outward, as shown in FIG. 21, beginning at approximately the location of flat region 814A to facilitate coupling and uncoupling from implant 10. The amount of curvature can allow for couplers 816A-818B to disengage from couplers 68A-70B. For example, the amount of curvature can be at least as much as the height of couplers 816A-818B, plus an additional amount to allow for removal from couplers 68A-70B.

Figure 22:
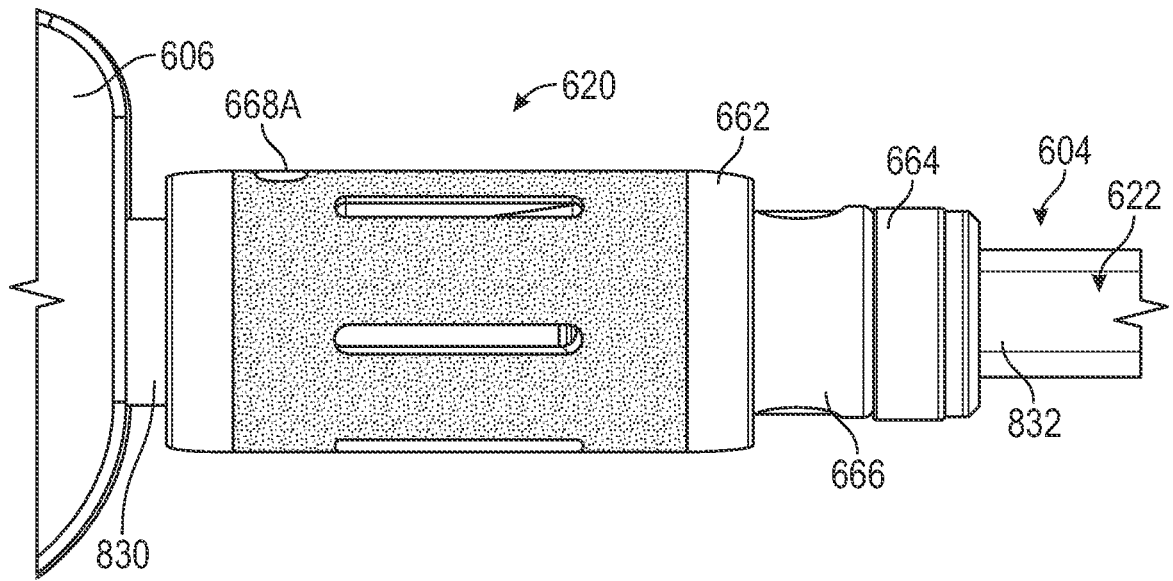
FIG. 22 is a side view of the coupling controller of FIG. 14 showing a control knob for the coupling arms.

FIG. 22 is a side view of coupling controller 620 of FIG. 14 showing control knob 662 for coupling arms 624A and 624B. Coupling controller 620 can comprise knob 662, piston 664, cover 666 and pins 668A and 668B. Shaft 622 can comprise first channel 680A and second channel 670B.

Shaft 622 can extend from body 606 at base 830. Shaft 622 can be stationary relative to body 606. Piston 664 can be slidably mounted to shaft 622 to move distally and proximally. Shaft 622 can comprise flat side 832, as well as an opposite flat side (not visible), along which piston 664 can slide. Flat side 832 and the opposing flat side prevent rotation of piston 664 about the axis of shaft 662. Knob 662 can be rotatably coupled with piston 664 such that rotation of knob 662 can cause proximal or distal translation of piston 664 along shaft 622.

Figure 23:
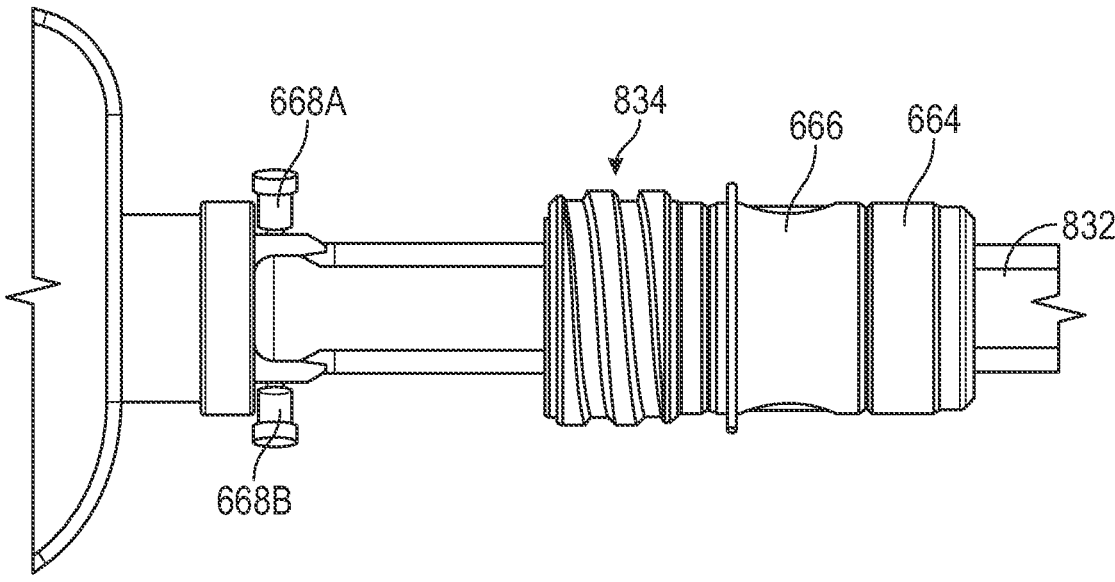
FIG. 23 is a side view of the coupling controller of FIG. 22 with the control knob removed to show a translation cam.

FIG. 23 is a side view of coupling controller 620 of FIG. 22 with control knob 662 removed to show piston 664. Pins 668A and 668B can be used to anchor knob 662 to shaft 622 so that knob 662 is prevented from translating along shaft 622. As can be seen in FIG. 25, knob 662 can include flange 846 that engages lip 848 of base 830 to prevent distal translation of knob 662. Pins 668A and 668B can prevent proximal translation of knob 662. However, pins 668A and 668B can be removed to facilitate disassembly of inserter 600. Piston 664 can include threading 834 that meshes with mating threading 836 (FIG. 25) on interior of bore 838 of knob 662. As such, rotation of knob 662 about the axis of shaft 622 can push or pull piston 664 via engagement of threading 834 and 836. Piston 664 can include cover 666 to allow access to ends of arms 624A and 624B where prongs 815A and 815B are located.

FIG. 24 is a side view of coupling controller 620 of FIG. 23 with access cover 666 removed from piston 664 to show springs 840A and 840B and balls 842A and 842, which can be used to bias cover 666 in place within piston 664. Seal 844 can additionally be placed between piston 664 and knob 662 to, for example, prevent disassembly of piston 664 from knob 662. Cover 666 can include lip 850 configured to be positioned distally of prongs 815A and 815B. Thus, when cover 666 is seated within window 852 of piston 664, lip 850 can prevent distal movement of arms 624A and 624B. However, when cover 666 is removed, arms 624A and 624B can be withdrawn from piston 664 in a distal direction along channels 670A and 670B.

As such, to assemble inserter 600, knob 622 can be placed over shaft 622 so flange 846 engages lip 848. Base 830 can be assembled with body 606. Pins 668A and 668B can be inserted to secure knob 622. Piston 664 can be assembled to knob 622 via rotation of knob 622 to thread ably engage with piston 664. Arms 624A and 624B can then be inserted into channels 670A and 670B until prongs 815A and 815B are visible in window 852. Cover 666 can then be placed in window 852 to secure arms 624A and 624B.

FIG. 25 is side cross-sectional view of coupling controller 620 of FIG. 22 showing engagement of control knob 622 and piston 664. As shown, threading 836 of knob 622 can engage threading of piston 624. Thus, knob 622 can be rotated in a fixed axial position about shaft 622 to cause pushing of piston 624 via the threaded engagement. Piston 624 can be prevented from rotation by engagement with flat sides 832 of shaft 622. Translation of piston 624 can cause a corresponding translation of arms 624A and 624B via engagement with prongs 815A and 815B.

Various Notes & Examples

Example 1 is an intervertebral implant comprising: a first cage; a second cage; a hinge connecting the first cage and the second cage at a first side of the intervertebral implant; a toggle joint connecting the first cage and the second cage at a second side of the intervertebral implant; and a wedge positioned between the first cage and the second cage and configured to translate from proximate the first side toward the second side to cause rotation about the hinge and initial expansion of the toggle joint.

In Example 2, the subject matter of Example 1 optionally includes wherein: the first cage comprises a first angled surface; and the second cage comprises a second angled surface opposing the first angled surface; wherein the wedge translates along the first and second angled surfaces to push the first and second cages away from each other.

In Example 3, the subject matter of Example 2 optionally includes a first stop surface extending inward from the first angled surface; and a second stop surface extending inward from the second angled surface; wherein the first and second stop surfaces are configured to inhibit further translation of the wedge along the first and second angled surfaces.

In Example 4, the subject matter of any one or more of Examples 1-3 optionally include wherein: the intervertebral implant is configured to rotate from a collapsed position to an expanded position; in the collapsed position the first cage and the second cage are within ten degrees of parallel; and in the expanded position the first cage and the second cage are angled relative to each other in a range of twenty-five to thirty-five degrees.

In Example 5, the subject matter of any one or more of Examples 1-4 optionally include wherein the wedge is accessible between the first cage and the second cage from the first side.

In Example 6, the subject matter of Example 5 optionally includes a screw mechanism configured to transition the expandable implant between an expanded position and a collapsed position, the screw mechanism comprising: a shaft having an outer threaded surface along which the wedge translates; a socket located at a first end of the shaft; and a pivot connected to the toggle joint at a second end.

In Example 7, the subject matter of Example 6 optionally includes wherein the shaft comprises: a first component comprising the outer threaded surface and the socket; and a second component threaded into the first component and including the pivot.

In Example 8, the subject matter of any one or more of Examples 1-7 optionally include wherein the toggle joint comprises: a first linkage extending from the first cage; and a second linkage extending from the second cage; and a pin coupling the first and second linkages.

In Example 9, the subject matter of Example 8 optionally includes wherein the first and second linkages are curved.

In Example 10, the subject matter of Example 9 optionally includes wherein: The toggle joint forms a rounded tip at the second side of the intervertebral implant in an expanded configuration; and the toggle joint forms a pointed tip at the second side of the intervertebral implant in a collapsed position.

In Example 11, the subject matter of any one or more of Examples 1-10 optionally include a plurality of arcuate slots located proximate the first side configured to couple to an inserter in a collapsed configuration and an expanded configuration.

Example 12 is a method of implanting an intervertebral implant, the method comprising: inserting the intervertebral implant into anatomy of a patient, the intervertebral implant comprising a first component rotatably coupled to a second component at a pivot point; operating a first expansion mechanism to rotate the intervertebral implant at the pivot point to expand the intervertebral implant to a first level; and operating a second expansion mechanism to rotate the intervertebral implant at the pivot point from the first level to a second level.

In Example 13, the subject matter of Example 12 optionally includes wherein operating the first expansion mechanism comprises: sliding a wedge along angled surfaces of the first and second components.

In Example 14, the subject matter of any one or more of Examples 12-13 optionally include wherein operating the second expansion mechanism comprises: expanding a toggle joint.

In Example 15, the subject matter of any one or more of Examples 12-14 optionally include wherein operating the first expansion mechanism and operating the second expansion mechanism comprise rotating a threaded fastener.

In Example 16, the subject matter of Example 15 optionally includes wherein rotating a threaded fastener comprises sequentially engaging the first expansion mechanism and then the second expansion mechanism.

In Example 17, the subject matter of any one or more of Examples 12-16 optionally include wherein inserting the intervertebral implant into anatomy of a patient comprises inserting the intervertebral implant into a spinal column such that the first component faces an inferior surface of a first vertebra and the second component faces a superior surface of a second vertebra adjacent the first vertebra.

Example 18 is a two-stage intervertebral implant comprising: an expandable cage comprising: an upper body; a lower body; and a pivot connecting the upper body and the lower body; a first expansion mechanism configured to pivot the upper body and the lower body at the pivot point in a first stage; and a second expansion mechanism configured to pivot the upper body and the lower body at the pivot point in a second stage beyond the first stage.

In Example 19, the subject matter of Example 18 optionally includes an actuation mechanism configured to sequentially operate the first expansion mechanism and the second expansion mechanism.

In Example 20, the subject matter of Example 19 optionally includes wherein: the first expansion mechanism comprises a wedge configured to slide against the upper body and the lower body to push apart the upper body and the lower body; the second expansion mechanism comprises a toggle joint configured to expand between the upper body and the lower body to push apart the upper body and the lower body; and the actuation mechanism comprises: a binding post fastener connected to the toggle joint; and a wedge threaded onto the binding post fastener and engaged with the upper and lower bodies.

Example 21 is an inserter device for a prosthetic implant, the inserter device comprising: an elongate rod extending from a proximal end to a distal end, the elongate rod comprising: an internal lumen extending between the proximal end and the distal end; and a first channel extending along an exterior of the elongate rod between the proximal end and the distal end; a first coupling arm comprising: an elongate shank configured to ride in the first channel; a distal coupling portion including a coupling feature configured for coupling to the prosthetic implant; and a proximal actuation portion; and an actuation mechanism coupled to a proximal end of the elongate rod and configured to move the first coupling arm within the first channel between a retracted position and an advanced position.

In Example 22, the subject matter of Example 21 optionally includes wherein elongate shank includes a pre-bend configured to bias the distal coupling portion away from the elongate rod.

In Example 23, the subject matter of Example 22 optionally includes wherein: the elongate shank is positioned such that the distal coupling portion extends out of the first channel such that: in the retracted position the distal coupling portion axially aligns with the first channel; and in the advanced position the distal coupling portion is displaced from the channel.

In Example 24, the subject matter of any one or more of Examples 21-23 optionally include wherein: the first channel comprises: a base extending along the elongate rod; and a pair of flanges overhanging the base; and the elongate shank is configured to slide along the base opposing the pair of flanges.

In Example 25, the subject matter of Example 24 optionally includes wherein the elongate shank comprises a T-shaped cross-section.

In Example 26, the subject matter of Example 25 optionally includes wherein the elongate shank comprises a segment proximal of the distal coupling portion comprising a rectangular cross-sectional profile.

In Example 27, the subject matter of any one or more of Examples 21-26 optionally include wherein the distal coupling portion comprises a pair of spaced apart tabs.

In Example 28, the subject matter of any one or more of Examples 21-27 optionally include wherein the actuation mechanism comprises: a knob rotatable about the elongate rod to push and pull the first coupling arm.

In Example 29, the subject matter of Example 28 optionally includes wherein the actuation mechanism further comprises: a piston configured to slide along the elongate rod in a non-rotatable fashion, the piston coupled to the first coupling arm; wherein the knob and the piston are disposed in threaded engagement such that rotation of the knob pushes and pulls the piston.

In Example 30, the subject matter of any one or more of Examples 21-29 optionally include a second coupling arm extending in a second channel of the elongate rod.

Example 31 is a push mechanism for dispensing a material from a handheld dispenser with a piston, the push mechanism comprising: a trigger configured to rotate about a pivot point; a first pawl configured to rotate on the trigger a first distance from the pivot point; and a second pawl configured to rotate on the trigger a second distance from the pivot point, wherein the second pawl is positioned relative to the first pawl to form a channel therebetween for pushing the piston in a longitudinal direction; wherein the first pawl and the second pawl are oppositely configured to interact with the channel.

In Example 32, the subject matter of Example 31 optionally includes wherein the first pawl and the second pawl are positioned above the pivot point.

In Example 33, the subject matter of any one or more of Examples 31-32 optionally include wherein: the first pawl faces toward the pivot point; and the second pawl faces away from the pivot point.

In Example 34, the subject matter of Example 33 optionally includes a first pushrod configured to engage with the first pawl; and a second pushrod configured to engage with the second pawl.

In Example 35, the subject matter of Example 34 optionally includes wherein the first pawl comprises: a first tang extending in the longitudinal direction; and a first rail extending alongside the first tang.

In Example 36, the subject matter of Example 35 optionally includes wherein the first pushrod comprises: a first tooth track comprising a plurality of positions configured to engage with the first tang; and a first channel configured to receive the first rail.

In Example 37, the subject matter of Example 36 optionally includes wherein the first pushrod comprises an opposite tooth track positioned diagonally across a cross-section of the first pushrod; and an opposite channel positioned diagonally across the cross-section of the first pushrod.

In Example 38, the subject matter of any one or more of Examples 34-37 optionally include wherein the second pawl comprises: a second tang extending in the longitudinal direction; and a second rail extending alongside the second tang.

In Example 39, the subject matter of Example 38 optionally includes wherein the second pushrod comprises: a second tooth track comprising a plurality of positions configured to engage with the second tan, and a second channel configured to receive the second rail.

In Example 40, the subject matter of any one or more of Examples 33-39 optionally include wherein the first pawl and the second pawl are biased toward the channel.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of a that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An intervertebral implant comprising:
a first cage comprising a first angled surface;
a second cage comprising a second angled surface opposing the first angled surface;
a drive shaft comprising a first shaft and a second shaft, the second shaft being threaded into the first shaft;
a hinge connecting the first cage and the second cage at a first side of the intervertebral implant;
a toggle joint connecting the first cage and the second cage at a second side of the intervertebral implant; and
a wedge having opposing surfaces and positioned between the first cage and the second cage and configured to translate from proximate the first side toward the second side,
wherein the wedge is positioned on the first shaft such that rotation of the first shaft causes the wedge to move closer to the second shaft and opposing surfaces of the wedge are pushed into the angled surfaces of the first and second cages to force the first cage and the second cage away from each other to cause rotation about the hinge and initial expansion of the toggle joint.

2. The intervertebral implant of claim 1, wherein:
the first shaft threadably engages the wedge such that the first shaft has an outer threaded surface along which the wedge translates and a threaded bore to engage a threaded exterior surface of the second shaft.

3. The intervertebral implant of claim 2, wherein the first cage comprises a first angled surface; and the second cage comprises a second angled surface opposing the first angled surface; wherein the wedge translates along the first and second angled surfaces to push the first and second cages away from each other and further comprising:
a first stop surface extending inward from the first angled surface; and
a second stop surface extending inward from the second angled surface;
wherein in a first stage expansion, the first and second stop surfaces are configured to inhibit further translation of the wedge along the first and second angled surfaces and the first and second shafts are configured to be disengaged from the toggle joint; and wherein in a second stage expansion, the first and second shafts are configured to engage and rotate the toggle joint while being disengaged from further translation of the wedge along the first and second angled surfaces.

4. The intervertebral implant of claim 1, wherein:
the intervertebral implant is configured to rotate from a collapsed position to an expanded position;
in the collapsed position the first cage and the second cage are within ten degrees of parallel; and
in the expanded position the first cage and the second cage are angled relative to each other in a range of twenty-five to thirty-five degrees.

5. The intervertebral implant of claim 1, wherein the wedge is accessible between the first cage and the second cage from the first side via a portal in the hinge that is configured to receive a driver to enable the driver to engage the first shaft.

6. The intervertebral implant of claim 5, wherein the first shaft has an outer threaded surface along which the wedge translates; the first shaft further comprising a socket located at a first end of the first shaft; and the second shaft threaded into the first shaft and including a pivot connected to the toggle joint at a second end.

7. The intervertebral implant of claim 6, wherein:
the wedge is provided with stops to engage stop surfaces of the first and second cages.

8. The intervertebral implant of claim 1, wherein the toggle joint comprises:
a first linkage extending from the first cage; and
a second linkage extending from the second cage; and
a pin coupling the first and second linkages.

9. The intervertebral implant of claim 8, wherein the first and second linkages are curved.

10. The intervertebral implant of claim 9, wherein:
the toggle joint forms a rounded tip at the second side of the intervertebral implant in an expanded configuration; and
the toggle joint forms a pointed tip at the second side of the intervertebral implant in a collapsed position.

11. The intervertebral implant of claim 1, further comprising a plurality of arcuate slots located proximate the first side configured to couple to an inserter in a collapsed configuration and an expanded configuration.

12. The intervertebral implant of claim 1, wherein a first expansion mechanism comprises the wedge to rotate the intervertebral implant at a pivot point to expand the intervertebral implant to a first level, wherein a second expansion mechanism comprises the toggle joint to rotate the intervertebral implant at the pivot point from the first level to a second level, and wherein the first and second expansion mechanisms are sequentially operated by a compound threading action between the second shaft threadably engaging an interior of the first shaft, an exterior of the first shaft threadably engaging the wedge.

13. The intervertebral implant of claim 12, wherein the pivot point connects proximal portions of the first and second cages, the first expansion mechanism rotates distal portions of the first and second cages of the intervertebral implant at the pivot point, and the second expansion mechanism rotates the distal portions of the first and second cages of the intervertebral implant at the pivot point from the first level to a second level, wherein, in the first level, the first expansion mechanism pivots the distal portions of the first and second cages at the pivot point without engagement of the second expansion mechanism, wherein, in the second level, the second expansion mechanism pivots the distal portions of the first and second cages at the pivot point without engagement of the first expansion mechanism, and wherein operating the first expansion mechanism and operating the second expansion mechanism comprise rotating a driver engaging the first shaft.

14. A two-stage intervertebral implant comprising:
an expandable cage comprising:
an upper body;
a lower body; and
a pivot connecting the upper body and the lower body;
a first expansion mechanism configured to pivot the upper body and the lower body at the pivot in a first stage;
a second expansion mechanism configured to pivot the upper body and the lower body at the pivot in a second stage beyond the first stage, and an actuation mechanism configured to sequentially operate the first expansion mechanism and the second expansion mechanism,
wherein the first expansion mechanism comprises a wedge configured to slide against the upper body and the lower body to push apart the upper body and the lower body;
wherein the second expansion mechanism comprises a toggle joint configured to expand between the upper body and the lower body to push apart the upper body and the lower body; and
wherein the actuation mechanism comprises a first shaft configured to engage a driver and a second shaft configured to threadably engage the first shaft, wherein the wedge engages the first shaft such that displacement of the first shaft relative to the second shaft causes displacement of the wedge, whereby opposing surfaces of the wedge engage corresponding first and second angled surfaces of the upper and lower bodies, respectively, to cause rotation and initial expansion of the toggle joint, and wherein engagement of the first shaft by the driver causes the first and second stages through sequential engagement of the first and second expansion mechanisms.

15. The two-stage intervertebral implant of claim 14, wherein the first expansion mechanism has a greater opening strength than the second expansion mechanism and is used to initiate expansion while the second expansion mechanism has a greater expansion height than the first expansion mechanism and is used to provide further expansion; and wherein:
the first and second expansion mechanisms comprise:
a binding post fastener connected to the toggle joint; and
the wedge threaded onto the binding post fastener and engaged with the upper and lower bodies.

16. The two-stage intervertebral implant of claim 14, wherein:
the first shaft threadably engages the wedge such that the first shaft has an outer threaded surface along which the wedge translates and a threaded bore to engage a threaded exterior surface of the second shaft; and
wherein the wedge translates along the first and second angled surfaces to push the upper and lower bodies away from each other.

17. The two-stage intervertebral implant of claim 16, further comprising:
a first stop surface extending inward from and transverse to the first angled surface; and
a second stop surface extending inward from and transverse to the second angled surface;
wherein, in the first stage, the first and second stop surfaces are configured to inhibit further translation of the wedge along the first and second angled surfaces and the first and second shafts are configured to inhibit rotation of the toggle joint; and
wherein, in the second stage, the first and second shafts are configured to rotate the toggle joint without further translation of the wedge along the first and second angled surfaces.

18. The two-stage intervertebral implant of claim 17, wherein the wedge is accessible between the upper and lower bodies from a proximal end via a portal in a hinge that is configured to receive the driver to enable the driver to engage the first shaft.

19. The two-stage intervertebral implant of claim 18, further comprising:
a screw mechanism configured to transition the implant between an expanded position and a collapsed position, the screw mechanism comprising the first shaft and the second shaft, the first shaft comprising a socket located at a first end of the first shaft to receive the driver, and the pivot connected to the toggle joint at a second end.

20. The two-stage intervertebral implant of claim 19, wherein opposing surfaces of the wedge each comprises an angled edge portion engaging a corresponding one of the first and second angled surfaces and a front portion engaging a corresponding one of the first and second stop surfaces, and wherein, in each of the opposing surfaces, the corresponding one of the first and second angled surfaces is transverse to the front portion.

* * * * *